(12) United States Patent
Chen et al.

(10) Patent No.: US 8,691,592 B2
(45) Date of Patent: Apr. 8, 2014

(54) MECHANICALLY ACTUATED DIAGNOSTIC DEVICE

(75) Inventors: Zongyuan Chen, Claymont, DE (US);
Haim H. Bau, Swarthmore, PA (US);
Michael Mauk, Greenville, DE (US);
Xianbo Qiu, Philadelphia, PA (US);
Jason Kwa, Wellesley, MA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 769 days.

(21) Appl. No.: 12/515,616

(22) PCT Filed: Dec. 14, 2007

(86) PCT No.: PCT/US2007/025699
§ 371 (c)(1),
(2), (4) Date: Aug. 23, 2010

(87) PCT Pub. No.: WO2008/076395
PCT Pub. Date: Jun. 26, 2008

(65) Prior Publication Data
US 2010/0304986 A1    Dec. 2, 2010

Related U.S. Application Data

(60) Provisional application No. 60/870,034, filed on Dec. 14, 2006.

(51) Int. Cl.
*G01N 1/28* (2006.01)
*G01N 35/00* (2006.01)
*B01L 3/00* (2006.01)
*B81B 5/00* (2006.01)
*G01N 33/00* (2006.01)

(52) U.S. Cl.
USPC ........... 436/180; 436/174; 422/504; 422/503; 422/502

(58) Field of Classification Search
USPC .......... 422/50, 68.1, 500, 501, 502, 503, 504, 422/506, 509, 512, 537; 436/174, 180
See application file for complete search history.

(56) References Cited

U.S. PATENT DOCUMENTS

| | | |
|---|---|---|
| 5,098,660 A | 3/1992 | Devaney, Jr. |
| 5,229,297 A | 7/1993 | Schnipelsky et al. |
| 5,422,271 A | 6/1995 | Chen et al. |
| 5,568,912 A | 10/1996 | Minami et al. |
| 5,575,632 A | 11/1996 | Morris et al. |
| 5,593,804 A | 1/1997 | Chemelli et al. |
| 5,811,296 A | 9/1998 | Chemelli et al. |
| 6,180,062 B1 | 1/2001 | Naka et al. |
| 6,300,138 B1 | 10/2001 | Gleason et al. |
| 6,645,758 B1 | 11/2003 | Schnipelsky et al. |
| 6,942,836 B2 | 9/2005 | Freudenthal et al. |

(Continued)

OTHER PUBLICATIONS

Niu, Xize et al. "Active microfluidic mixer chip." Applied Physics Letters (2006) 88 153508.*

(Continued)

*Primary Examiner* — Christopher A Hixson
(74) *Attorney, Agent, or Firm* — Baker & Hostetler LLP

(57) ABSTRACT

Disclosed are mechanically-actuated devices for transporting fluids within a microfluidic circuit and performing diagnostic operations on a sample. Also disclosed are related methods for performing sample analysis effected by the motion of an actuator proximate to a microfluidic system.

13 Claims, 31 Drawing Sheets

(56) References Cited

U.S. PATENT DOCUMENTS

| | | |
|---|---|---|
| 2001/0052460 A1 | 12/2001 | Chien et al. |
| 2003/0152994 A1 | 8/2003 | Woudenberg et al. |
| 2005/0054113 A1 | 3/2005 | Bedingham et al. |
| 2005/0123454 A1 | 6/2005 | Cox |
| 2006/0002827 A1* | 1/2006 | Curcio et al. ............ 422/103 |
| 2009/0186357 A1 | 7/2009 | Mauk |
| 2009/0226911 A1 | 9/2009 | Mauk |

OTHER PUBLICATIONS

Woias, Peter. "Micropumps—past, progress, and future prospects." Sensors and Actuators B (2005) 105 28-38.*

Weibel, Douglas B. et al. Anal. Chem. (2005) 77 4726-4733.*

Corstjens et al., "Use of Up-Converting Phosphor Reporters in Lateral-Flor Assays to Detect Specific Nucleic Acid Sequences: A Rapid, Sensitive DNA Test to Identify Human Papillomavirus Type 16 Infection", Clinical Chemistry, 2001, 47, 10, 1885-1893.

Findlay et al., "Automated Closed-Vessel System for In Vitro Diagnostics Based on Polymerase Chain Reaction", Clinical Chemistry, 38, 9, 1927-1933.

Product Brochure on Diskhaler, Mar. 2006, Retrieved from the Internet at URL http://www.relenza.com/hcp/relenza-diskhaler-delivery-system.html on Nov. 5, 2009.

U.S. Appl. No. 12/535,718, filed Aug. 5, 2009, by Bau et al.

Weibel, D.B. et al., "Torque-Actuated Valves for Microfluidics", Anal Chem, 2005, 77, 4726-4733.

* cited by examiner

Mouted-on-Chip Regent Supply Module
LDPE-based supply module

Quick thermal banding top film to bottom base

Pouch tops rise as individual reagents are injected from ports on bottom

Ports are sealed on the bottom surface with aluminum foil tape

Assembled Cassette

Actuator (top view)

Polyethylene cassette (top view)

Polycarbonate cassette (bottom view)

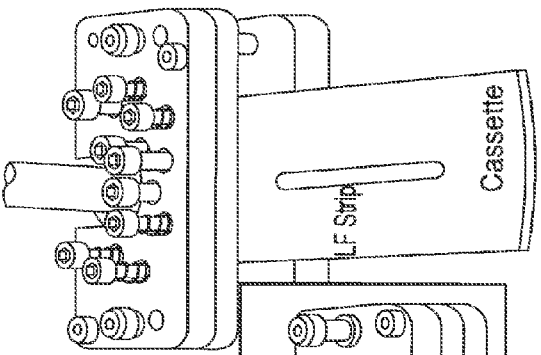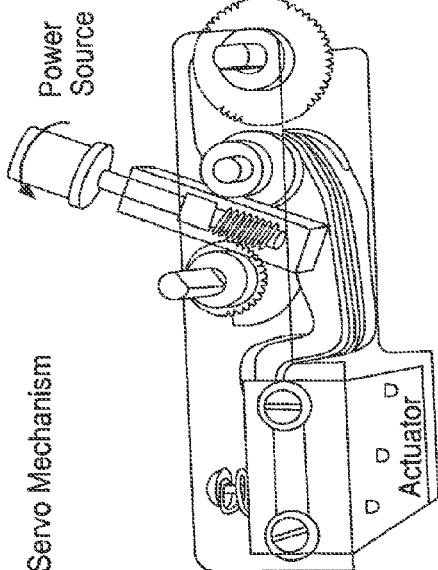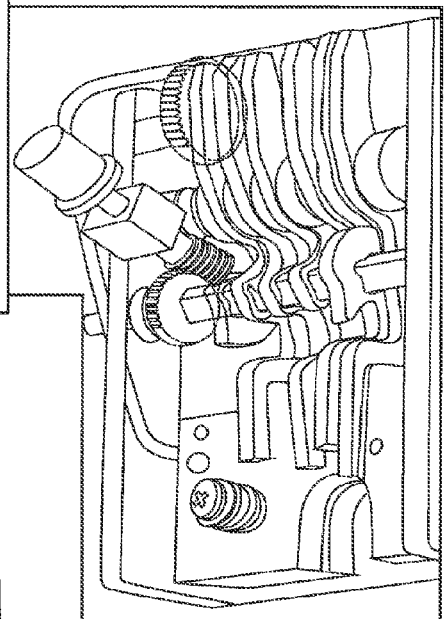

MECHANICALLY ACTUATED DIAGNOSTIC DEVICE

CROSS-REFERENCE TO RELATED APPLICATIONS

This application is the National Stage of International Application No. PCT/US2007/025699, filed Dec. 14, 2007, which claims the benefit of U.S. Provisional Application No. 60/870,034 filed Dec. 14, 2006, the disclosure of which is incorporated herein by reference in its entirety.

STATEMENT OF GOVERNMENT RIGHTS

This invention was made with U.S. Government support. The Government may have certain rights in the invention under National Institutes of Health grant number NIH/NIDCR UO1DE01785.

FIELD OF THE INVENTION

The present invention relates to the field of pneumomechanical fluid handling systems. The present invention also relates to the field of diagnostic devices.

BACKGROUND OF THE INVENTION

The advancement of techniques and methods for detection of biological and non-biological samples for pathogens, drugs, toxins, and the like provides important tools for clinical practitioners as well as for military and paramedic personnel. Such techniques and methods for pathogen detection have additional application to fields other than medicine, including testing food, beverages, and consumer goods for pathogens or contaminants.

Detection techniques typically involve subjecting a sample to a prescribed sequence of fluid transfer, mixing, reaction, and detection steps, all within a contained fluidic system.

Certain of these devices are limited in application, however, because they may not be ideal for transport to and through a rugged field environment where pathogen testing may be necessary. Other devices are complex and are reliably operated only by trained personnel and may be slow to produce results. Accordingly, such systems are not well-suited for use by personnel lacking specialized training or by personnel who may be called upon to perform pathogen testing while under duress.

Further, existing detection systems arrange system components in a linear fashion wherein elements are only accessed sequentially, and may not be capable of effecting more intricate fluid actuation schemes, such as repeatedly transporting fluid between two or more components of a fluidic circuit before then transporting the fluid to subsequent downstream components. This limitation reduces the utility of existing systems in that intricate fluid transport schemes may be necessary to detect certain pathogens.

Accordingly, there is a need for robust devices capable of assaying samples for pathogens, drugs, toxins, bacteria, viruses, medical abnormalities, and the like. Because pathogen detection schemes include multiple mixing, washing, and reacting steps, there is a related need for an apparatus capable of actuating complex schemes of fluid motion. The value of such a device would be further enhanced if its use did not require a specially trained operator.

SUMMARY OF THE INVENTION

In meeting the described challenges, the present invention provides a fluid processing system, comprising a first component comprising a substrate comprising first and second surfaces; a fluid reservoir disposed at the first surface of the substrate, a deformable capping layer sealing the fluid reservoir, the deformable capping layer being capable of deformation so as to reduce the volume within the fluid reservoir; a reservoir aperture capable of placing the fluid reservoir into fluid communication with the environment exterior to the first component; a sealant layer sealing at least a portion of the reservoir aperture against the environment exterior to the first component; and a second component, the second component comprising a substrate comprising a fluidic element.

The present invention also provides a sample processing system, comprising a component comprising at least one fluidic element sealed by a deformable sealing layer; and a moveable actuator residing proximate to the component, at least a portion of the actuator capable of motion relative to the component, the actuator comprising one or more actuator portions capable of actuating at least one fluidic element, the one or more actuator portions being arranged such that movement of the actuator effects a prescribed sequence of actuations of the deformable sealing layer, of one or more fluidic elements, or both, and movement of the actuator being capable of effecting fluid motion within at least a portion of the component.

Further disclosed is a method for analyzing a sample, comprising placing the sample into a component comprising two or more fluidic elements in fluid communication with one another, the one or more fluidic elements being surmounted by a deformable layer; controllably subjecting at least a portion of the sample to one or more processing steps effected by the movement of an actuator relative to the first substrate, the actuator comprising one or more physical features arranged so as to effect a predetermined schedule of processing steps when the actuator is moved relative to the component, one or more of the processing steps comprising transport of the sample from one fluidic element to another, and analyzing the sample for the presence of one or more analytes.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 7b depicts the fluid reservoirs disposed on the cassette of FIG. 7a;

FIG. 7c depicts the fluid connectors, fluidic conduits, and capture zones embedded in a lateral flow strip for the cassette of FIG. 7a;

FIG. 18b illustrates the device of FIG. 18a wherein a sample cassette has been loaded into the device of FIG. 18a;

FIG. 18c illustrates an alternative embodiment of the device shown in FIG. 18a, further comprising a driveshaft in communication with the camshaft;

FIG. 18d illustrates the device of FIG. 18c, viewed from above;

FIG. 18e illustrates the actuator of the device illustrated in FIG. 18d;

FIG. 18f illustrates a cassette positioned within the actuator of the device illustrated in FIG. 18a;

FIG. 18g illustrates a cassette inserted within the actuator of FIG. 18f, further illustrating a sample collector mated to the cassette;

DESCRIPTION OF ILLUSTRATIVE EMBODIMENTS

Terms

Figure 1A:
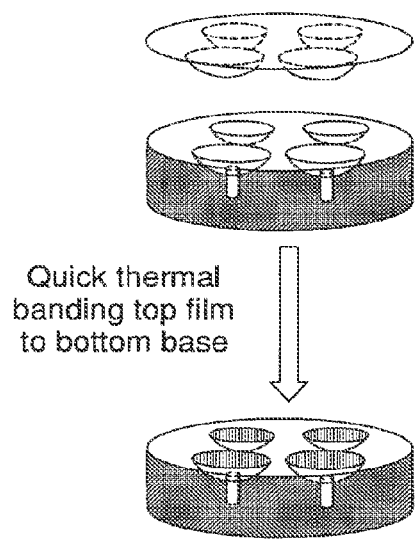
FIGS. 1a, 1b, and 1c illustrate a representative set of fluid reservoirs constructed on a substrate.

As used herein, the term "blister" refers to a fluid reservoir capped by a membrane that is flexible or deformable, or both. In some configurations, a blister refers to a chamber or pocket formed in a single substrate. As a non-limiting example of such a configuration, a bubble formed in a sheet of polymer would be considered a blister. Blisters may also be dome- or pouch-shaped in form.

As used herein, the term "cassette" refers to a component or assemblage that, in certain embodiments, comprises one or more fluid-containing blister reservoirs, valves, or both. A cassette may also include one or more fluidic channels—described elsewhere herein—and, in some cases, may include one or more ports or vents that place portions of the cassette into communication with the environment exterior to the cassette. A cassette may also be pre-loaded with one or more reagents—in fluid form or dried form.

As used herein, the term "actuator" refers to a device or object that, when operated, exerts a force on an object, activates a switch, deactivates a switch, and the like. As a non-limiting example, a spring-loaded lever capable of turning on a switch when the lever is pulled back and released would be considered an actuator.

As used herein, the term "actuate" means to move, position, exert a force on, to turn on, to turn off, to compress, to deform, to depress, to lift, to open, to close, and other similar actions. In one non-limiting example, actuating a deformable layer means to press on the layer. As another non-limiting example to actuate a heater means to turn the heater on, by activating a switch, for example. In a further example, actuating a blister reservoir means to press on the reservoir such that at least a portion of the fluid residing within the reservoir is forced out of the reservoir.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention that are, for clarity, described herein in the context of separate embodiments, may also be provided in combination in a single embodiment. Conversely, various features of the invention that are, for brevity, described in the context of a single embodiment, may also be provided separately or in any subcombination. Further, references to values stated in ranges include each and every value within that range.

In a first aspect, the claimed invention provides fluid processing systems. Such systems include a first component that includes a substrate comprising first and second surfaces, and a fluid reservoir disposed at the first surface of the substrate. The systems also have a deformable capping layer sealing the fluid reservoir, the deformable capping layer being capable of deformation so as to reduce the volume within the fluid reservoir. Also present is a reservoir aperture positioned and dimensioned so as to place the fluid reservoir into fluid communication with the environment exterior to the first component; a sealant layer sealing at least a portion of the reservoir aperture against the environment exterior to the first component. The systems additionally include a second component, the second component including a substrate comprising a fluidic element.

One or both of the components may include a connector capable of placing the reservoir of the first component into fluid communication with a fluidic element of the second component. The fluidic element of the second substrate may include a connector capable of penetrating the sealant layer of the first component to as to place the fluidic element of the second component in fluidic communication with the fluid reservoir of the first component when properly positioned relative to the first component. Suitable connectors are described further herein.

The substrates of the first and second components are suitably fashioned from a polymer, a metal, a metal oxide, a rubber, a ceramic, a glass, and the like. Glass and polycarbonate are both considered especially suitable substrates, but other polymers may be optimal for a given application or a given user's needs. A substrate material may be chosen based on its suitability to particular methods of processing or by its resistance to certain chemical agents or biological materials. Suitable substrates will be apparent to those having ordinary skill in the art, and may, in some cases, be dictated by the user's needs.

Substrates may have a thickness in the range of from about 500 μm to about 10 mm, or from about 1 mm to about 5 mm, or even of about 2 mm. The thickness of a given substrate will be dictated by the needs of the user and the parameters of a particular application and may depend on mechanical stresses the substrate may experience during the course of usage.

A fluid reservoir may be a blister, a dome, a bulge, a capsule, a packet, a pouch, and the like. Blisters are considered particularly suitable forms of reservoirs. Reservoirs may be formed on the surface of a substrate, but may also, in some embodiments, include one or more depressions formed in a surface of the substrate. In some embodiments, a reservoir may be formed by capping both ends of a hole or channel extended through a substrate. A reservoir may also be formed along an edge of a substrate as well as along the upper or lower surfaces of a substrate.

The volume of a given reservoir may vary depending on the user's needs and constraints. Suitable reservoirs may have a volume in the range of from about 1 μl to about 5 ml, or from 5 μl to about 1 ml.

A fluid reservoir preferably contains one or more fluids. Suitable fluids include water, solutions of reagents, acids, bases, buffers, suspensions, labels, dyes, biological materials, nucleotides, lysing agents, particles, air, gas, or any combination thereof. The fluid contained within a reservoir will be dictated by the user's needs. Preferably, the substrate material, the deformable capping layer—described elsewhere herein—and the fluid are chosen such that the fluid is inert or relatively inert to those materials it may contact.

In alternative embodiments, a reservoir may be empty or filled with air or a gas, depending on the user's needs. In some configurations, an empty reservoir may be used to hold sample fluid, a reaction mixture, a waste fluid, excess fluid.

The deformable capping layer of the claimed invention may be a polymer, an elastomer, a rubber, a metal, a metal oxide, or any combination thereof. In some embodiments, the capping layer is a laminate comprising multiple materials. The layer may be bonded to the first surface of the substrate of the first component, or, in some embodiments, may be bonded to the substrate that borders the reservoir. As a non-limiting example, the layer may be bonded to the lip of a depression fashioned in a substrate so as to create a domed reservoir.

In other embodiments, e.g., FIG. 1a, the capping layer is bonded across the substrate, including the regions of the substrate between separate reservoirs. The deformable layer may be capable of reversible or irreversible deformation. Reversible deformable materials are suitable for embodiments where the capping layer may be actuated multiple times during the course or a reaction or assay.

The described reservoir aperture is preferably a channel or conduit extending from the reservoir to the environment exterior to the first component. In one embodiment, shown in FIG. 1a, the aperture extends from the base of the reservoir through the substrate to the environment exterior to the lower face of the substrate shown in that figure. In other embodiments, the aperture may curve or bend from the base of the reservoir on the first surface of a substrate so as to connect the reservoir to the environment exterior to the first face of that substrate. Reservoir apertures may have characteristic diameters in the range of from about 10 μm to about 1 mm, or from about 200 μm to about 500 μm. The apertures are suitably circular in cross-section, but may have cross-sections that are square, triangular, or polygonal. An aperture may have a constant cross-section along its length, but may also have an increasing or decreasing cross section as necessitated by the user. In some configurations, a reservoir may comprise two or more apertures; such apertures may be useful in venting air when the reservoir is filled.

Figure 1B:
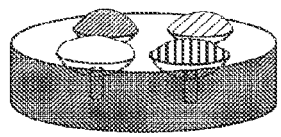
Figure 1C:
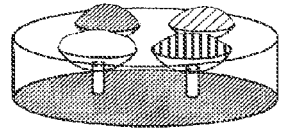

As further depicted in FIG. 1b, a reservoir may be filled by injecting fluid into the reservoir by way of the reservoir aperture. After such injection, the reservoir may be sealed by a sealant layer, as depicted in FIG. 1c.

Suitable sealant layers include polymers, rubber, metals, metal oxides, waxes, aluminum foils, adhesive tapes, or any combination thereof. In some embodiments, the sealant layer is chosen so as to form a leak-proof seal when penetrated by a connector, such as a needle or lance. Suitable materials for these embodiments include waxes and polymers.

In some embodiments, the sealant layer is selected from a set of frangible materials so as to break into fragments when forcibly contacted or struck. The sealant layer may include one or more materials or be a composite, and, in some embodiments, may include two or more layers of two or more materials so as to meet the user's needs. In some embodiments, the deformable capping layer, the sealing layer, and the substrate are formed of the same material. Such embodiments include fluid-filled reservoirs and other fluidic channels that are all formed within a pouch that is comprised of a single material.

Fluidic elements include a number of structures, including conduits, chambers, valves, reservoirs, mixing zones, channels, vents, valves, and the like. Fluidic elements may also include empty or air-filled reservoirs, which may be capped by a deformable layer. Two or more fluidic elements may suitably be combined, for example, in a channel-valve assembly. It is contemplated that both the first and second components may include one or more fluidic elements; exemplary embodiments are described in more detail elsewhere herein.

Fluidic elements may, in some embodiments, be sealably covered by a deformable layer. Such layers are described elsewhere herein. In one non-limiting example, a channel may be covered by a deformable layer such that depression of the layer reduces the effective volume within the channel and expels fluid residing within the channel when the layer is depressed. By actuating one or more valves that control entry and exit of fluid from the channel, the user may effect fluid flow in a specific direction by controllably actuating the valves and depressing the deformable layer atop the channel.

Valves may include a deformable layer, a hatch, a septum, a butterfly valve, a diaphragm valve, a ball valve, or any combination thereof. It is contemplated that a valve may be actuated by the accumulation of fluid pressure on one side of the valve or by application of external force.

Valves may be capable or reversible or irreversible operations, and may be one-way or two-way valves. In embodiments that may require prevention of fluid backflow from one fluidic element into another, an irreversible or one-way valve may be used.

In some embodiments, a fluidic element may incorporate a frangible seal. In such embodiments, the seal may be breached by the application of force. As a non-limiting example, a component may include a chamber of fluid bounded at one end by a frangible seal and capped by a deformable sealing layer. When pressure is applied to the sealing layer, the frangible seal located below may rupture so as to liberate the contents of the formerly-sealed channel and to place those contents into fluid communication with other channels or conduits that were previously blocked by the seal.

Figure 2A:
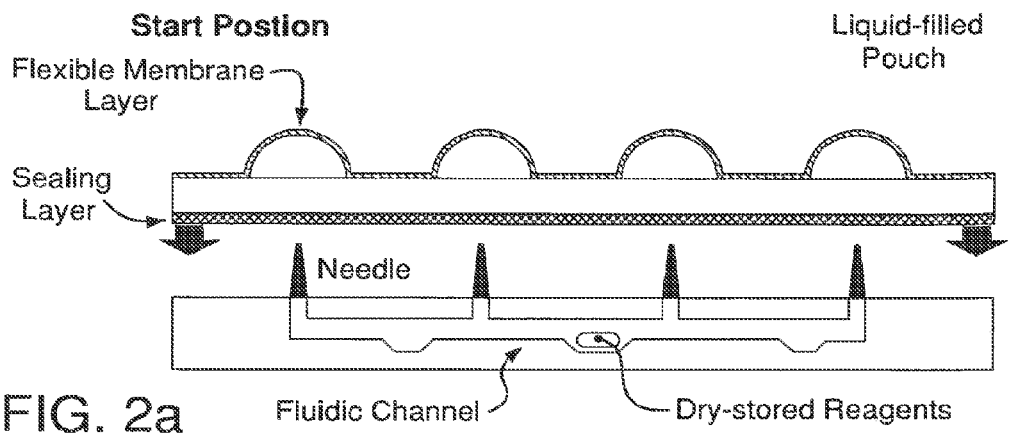
FIG. 2a depicts a blister pack reservoir and a fluidic channel comprising needle connectors.

Connectors for placing a fluid reservoir into fluid communication with another fluid element include hollow lances, pipettes, cannulas, needles, and the like. A sample needle-type connector is shown in FIG. 2a.

Connectors may be of varying size, and their dimensions will suitably be dictated by the dimensions and characteristics of any layers or membranes through which the connectors may be inserted. Connectors are preferably chosen and shaped on the basis of their ability to penetrate the sealant layer. The combination of connectors and sealant layer may be chosen based on the ability of the combination to form a leak-proof seal between the connector and any fluidic element into which it penetrates through the sealant layer.

A connector may be formed from a metal, a polymer, a metal oxide, and the like. A connector may be formed from the same material as a substrate on which the connector is disposed, or may be made from a different material than the substrate. A connector may extend outward from a substrate or—in an embodiment where a protruding connector is undesirable—the connector may be disposed in a recess or depression formed in the substrate.

In some embodiments, the fluid processing system further includes an analysis device, suitably capable of fluid communication with the fluid reservoir. Such a device can include a microarray, a microbead, multiple beads bearing different functionalities, a cellulose-based strip, a capture zone, or a combination of any of these. Analyzers are typically chosen for their ability to detect one or more chemical or biological species. Analyzers may be chosen for their ability to process or detect proteins, antigens, or free floating nucleic acids, or any of the preceding. The analyzer suitable for a given application will be apparent to the user having ordinary skill in the art, and is not limited to the analyzers listed herein.

In some embodiments, the system further includes an inlet port capable of placing a fluid reservoir, a fluidic element, or both, in fluid communication with the environment exterior to the fluid processing system. Such ports may be included in either the first or second components of the claimed system. As an example, an inlet port may be fashioned so as to allow introduction of a sample into the system into a chamber that is itself connected to a channel and a fluid reservoir.

Exemplary, non-limiting embodiments of the claimed systems are illustrated in FIG. 1a and 1b. In those figures, reservoirs are created by bonding a deformable top layer to a substrate having four depressions, thereby forming four discrete reservoirs on the substrate. Each of the reservoirs also includes an aperture, placing the reservoir in fluid communication with the lower surface of the substrate. The reservoirs may then be filled with liquid, FIG. 1c, and sealed by a sealing layer so as to form independent, sealed reservoirs on the substrate.

Figure 2B:
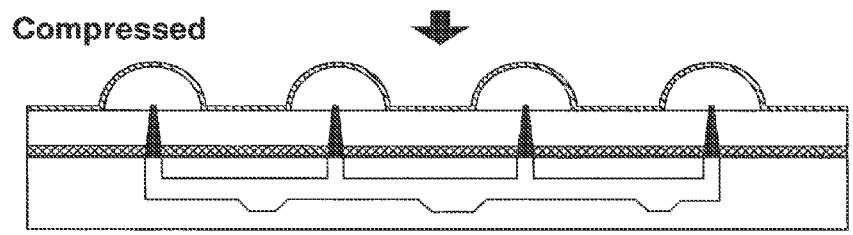
FIG. 2b depicts a side view of the blister pack and fluidic channel of FIG. 2a, following the insertion of the connectors into the blister packs.
Figure 2C:
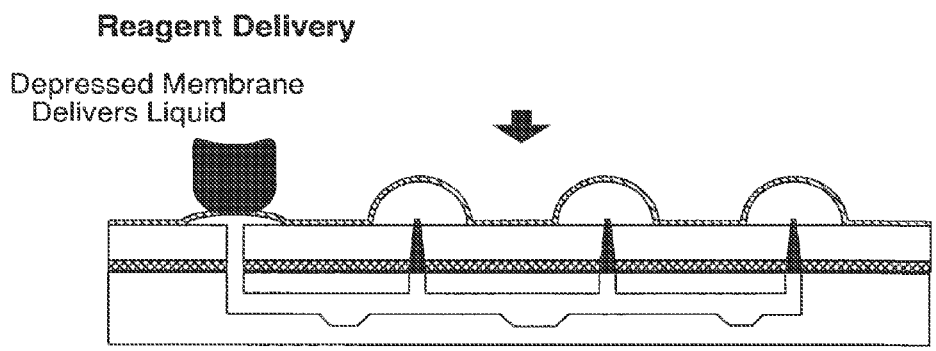
FIG. 2c depicts depression of one of the blister reservoirs of FIG. 2a and the movement of fluid displaced from that reservoir.

Another embodiment of the claimed system is depicted in FIG. 2a, FIG. 2b, and FIG. 2c. FIG. 2a depicts a first component including several fluid-filled reservoirs sealed by a sealing layer. In this embodiment, each of the reservoirs has a reservoir aperture placing the reservoir into fluid communication with the environment below the first substrate. FIG. 2a also includes a second substrate having a channel including several hollow needles, with dry-stored reagents residing within the channel. One example of dry-stored reagents is set forth in "Reaction Chamber Having Pre-Stored Reagents," U.S. Application 61/012,669, filed Dec. 10, 2007, the entirety of which is incorporated by reference herein.

In FIG. 2b, the second substrate is positioned relative to the first substrate such that the needles pierce the sealing layer of the first substrate, thus placing the reservoirs in fluid communication with the channel of the second substrate, and, by extension, with each other.

Figure 2D:
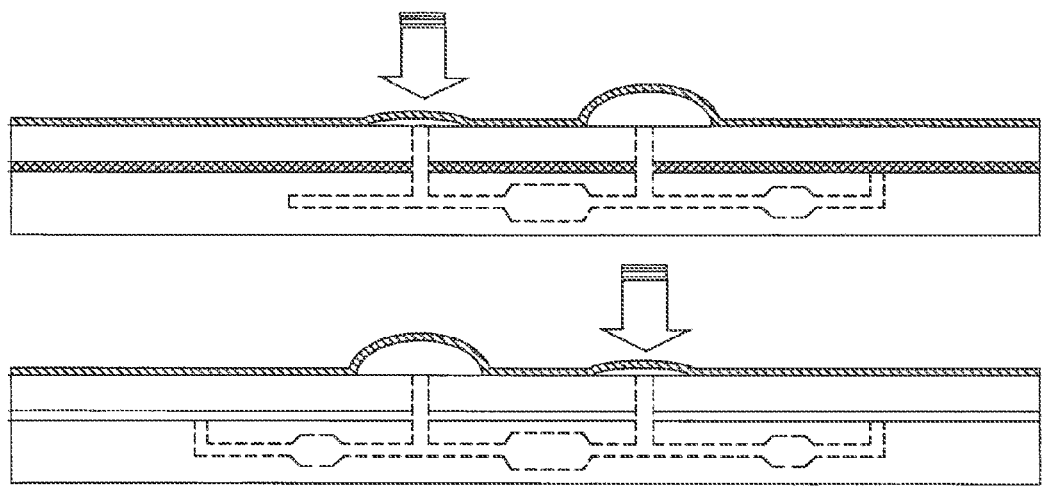
FIG. 2d illustrates hydration and homogenation of dry-stored reagents.

In FIG. 2c, downward pressure is exerted on one of the reservoirs, forcing the fluid contained within that reservoir out through the reservoir aperture and into the channel of the second substrate. There, the fluid passes along the channel and, if the dried reagents are suitably chosen, the fluid may rehydrate the reagents. More than one reservoir may be depressed, as shown in FIG. 2d, thus effecting a reciprocating fluid mixing effect. The sequence of reservoir depression will be dictated by the needs of the user. A user having ordinary skill in the art will be able to identify the necessary sequence of depressing and pumping actions needed to effect a certain sequence of fluid transport steps. While the embodiment shown includes only two components, the claimed invention includes embodiments having three or more components capable of mating together to form an integrated device.

Figure 7A:
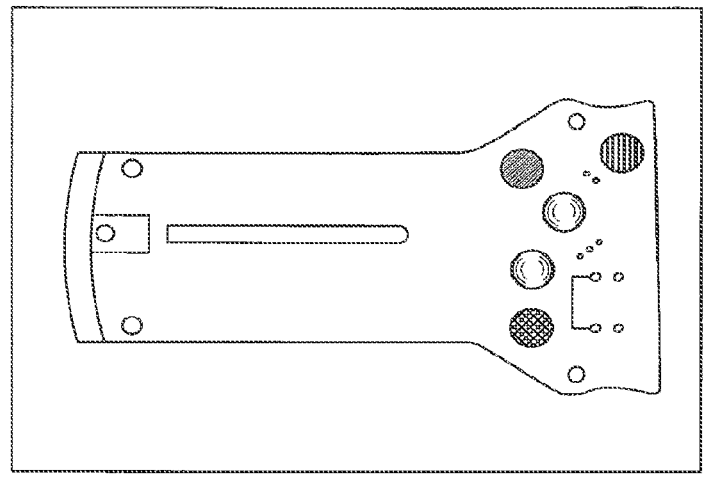
FIG. 7a depicts a cassette for processing of immunoassays or free-floating nucleic acids.
Figure 7B:
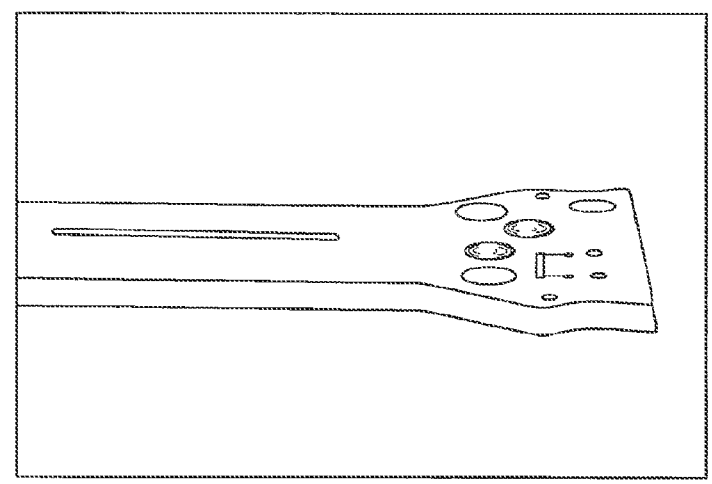
Figure 7C:
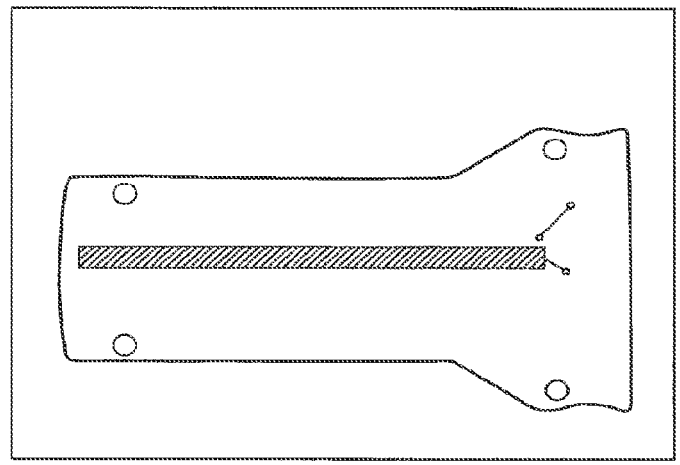
Figure 7D:
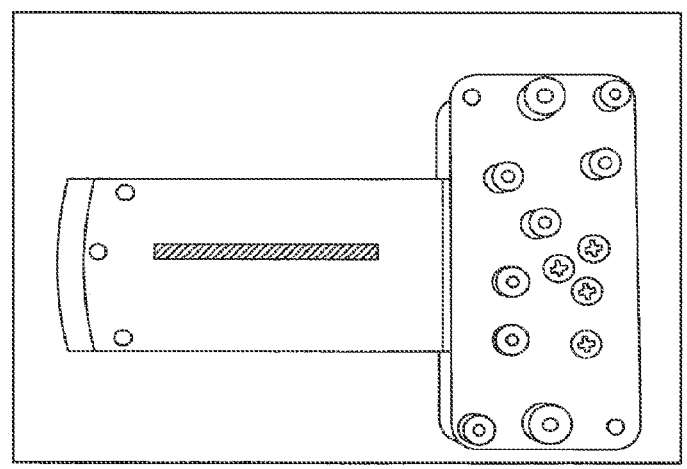
FIG. 7d illustrates the cassette of FIG. 7a inserted into an actuator.

FIG. 7a shows a sample embodiment of the claimed system, showing a cassette for immunoassay processing. The cassette consists of two mated components. The first of these two components, FIG. 7b, comprises reservoirs for buffer, wash solution, and labels, a sample-metering chamber, and valves. The second component, FIG. 7c, is that part of the cassette that contains fluidic conduits and lances that allow communications between the various reservoirs of the part shown in FIG. 7b and a lateral flow strip with one or more capture zones for the immobilization of selected analytes. FIG. 7d shows the cassette inserted into an actuator that facilitates the actuation of the various reservoirs and valves.

Figure 8:
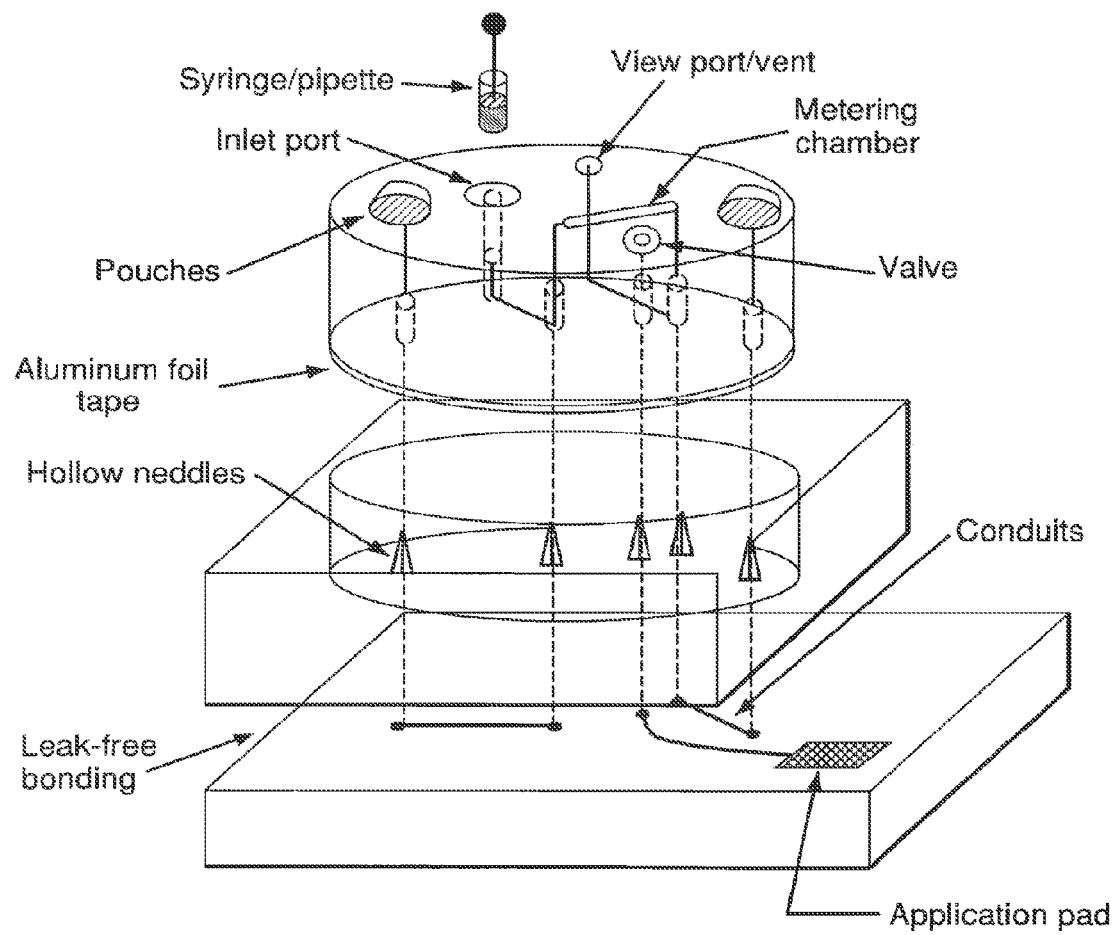
FIG. 8 depicts an illustrative example of a sample introduction module containing a metering chamber and facilitating the mixing of the sample with buffer.

FIG. 8 shows a schematic view of an alternative embodiment of the cassette of FIGS. 7a-7d. As shown, the first substrate includes several pouch reservoirs and a sample inlet, into which inlet sample is injected or otherwise introduced. The first substrate may be mounted onto the second, connector-comprising substrate, thus forming a connection between the pouches and channels of the first substrate and the channels of the second substrate. The first substrate also includes a viewing port and vent, which permit, respectively, the visual inspection of a sample contained within the system and also the escape of air or excess fluids and reagents.

Figure 9:
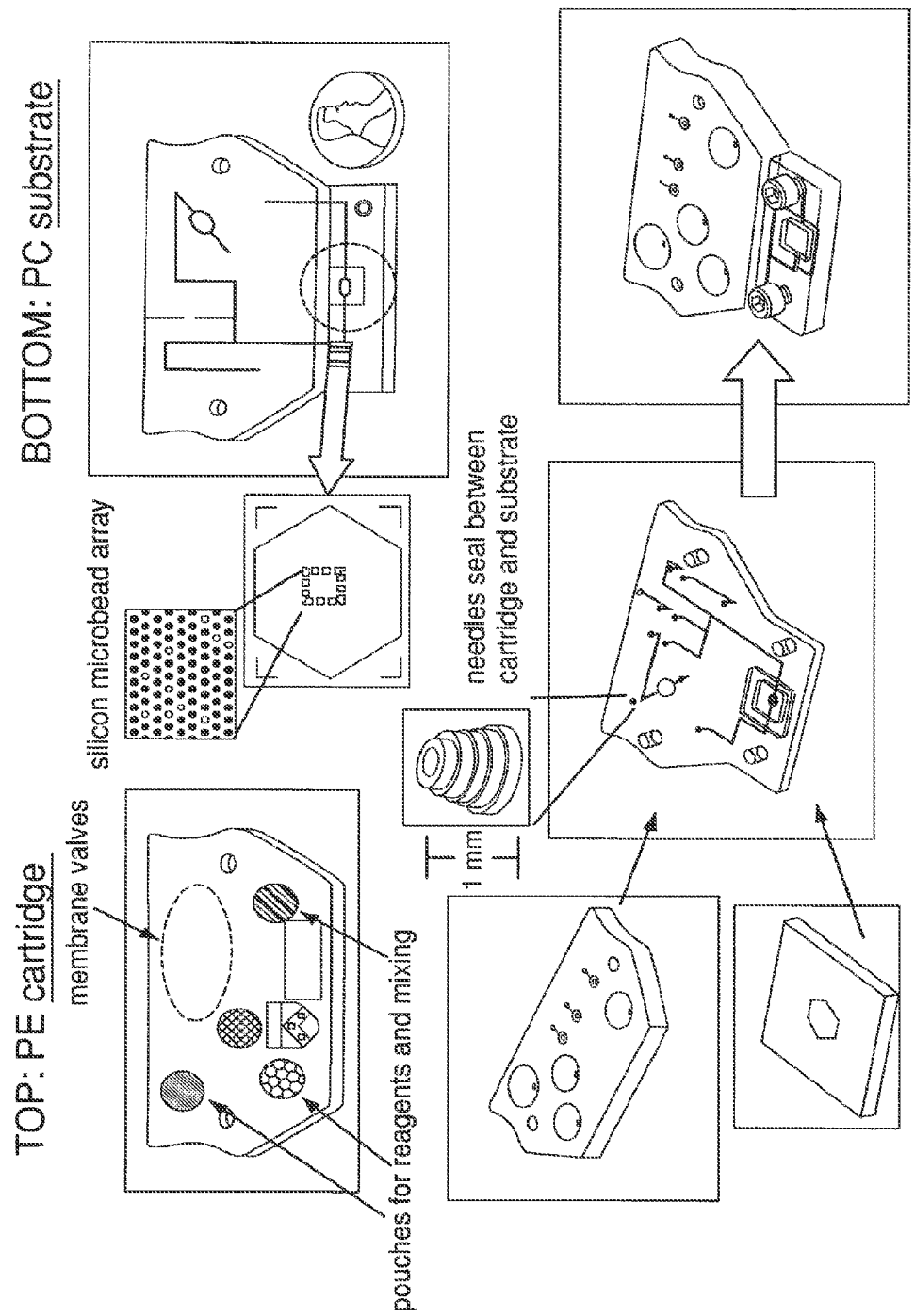
FIG. 9 illustrates a sample cassette having a bead array for the capture of target analytes.

FIG. 9 depicts a cassette for the detection of target analytes in a sample, which cassette includes of two components. A first component includes several fluid-filled reservoirs and several membrane valves. The reservoirs are filled with buffer, wash solution, and labels. The valves may be apertures extending from one surface of the substrate to the other, that are capped by a membrane that is deformed or deflected so as to open or close the valves. Also illustrated in FIG. 9 is a second component that includes a network of channels and chambers, which component also includes a microbead array in which beads are differentially functionalized with different proteins used for capturing target molecules or species that are formed by subjecting a sample to one or more processing steps. A hollow lance-type connector is also shown, which connector converts the channels and detector of the second component to the fluid reservoirs and valves of the first component.

Figure 10:
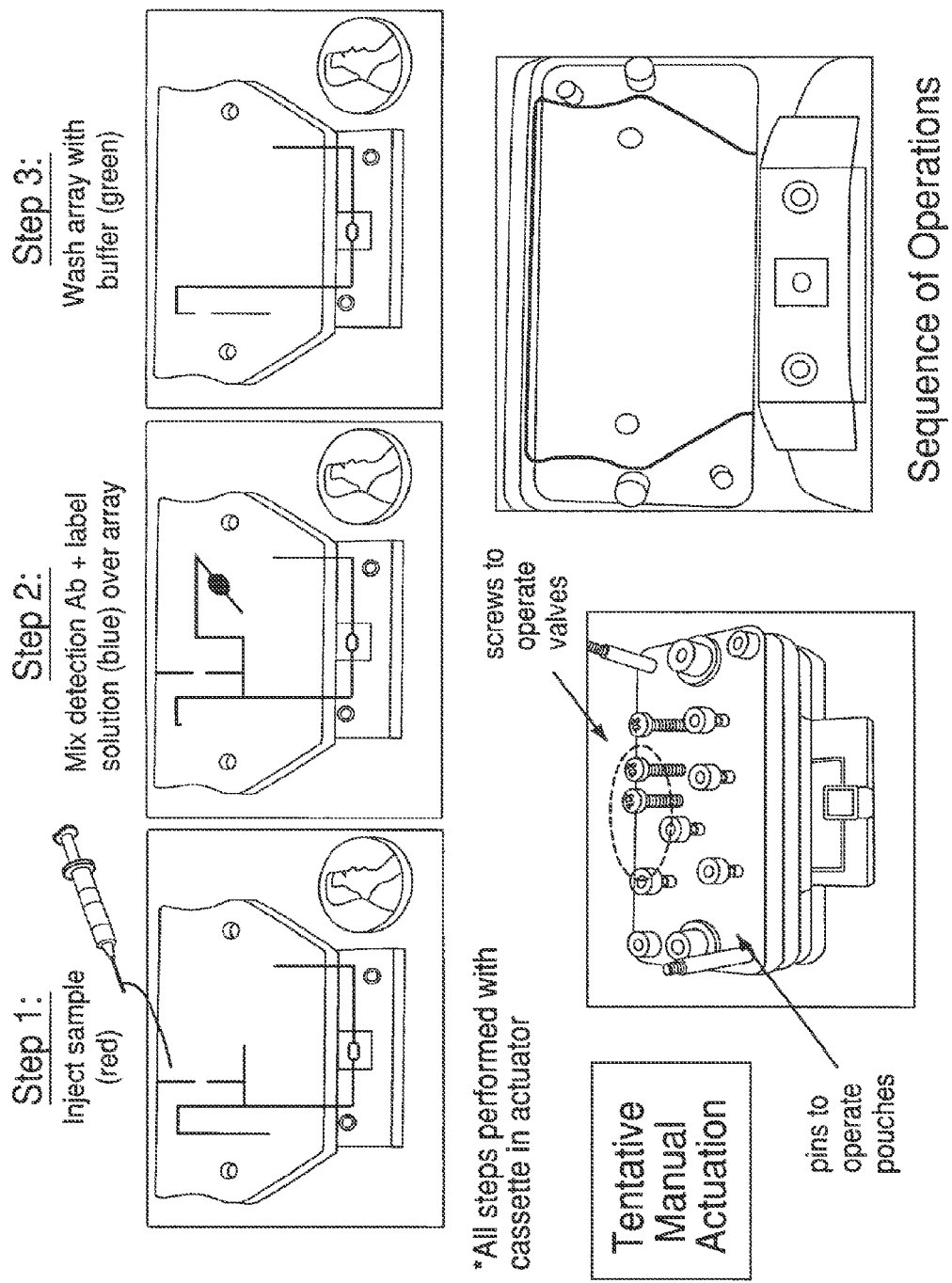
FIG. 10 illustrates fluid flow within the cassette of FIG. 9.

FIG. 10 depicts the process steps that are performed in one embodiment of the invention. Once the cassette is inserted into the actuator, the sample followed by a solution of labels flows through the bead array. Actuation of the pouches facilitate a back and forth motion of the sample and labels through the capture zone—a bead array, in this embodiment—to assure high mass transfer. Subsequently, wash solution is transmitted to remove unbound labels.

Following sample binding to the bead array, the labels on the sample are exited by illumination at their excitation wavelength. Beads that bind captured analytes then emit light that allows for detection of the presence and quantity of target analytes.

Figure 12A:
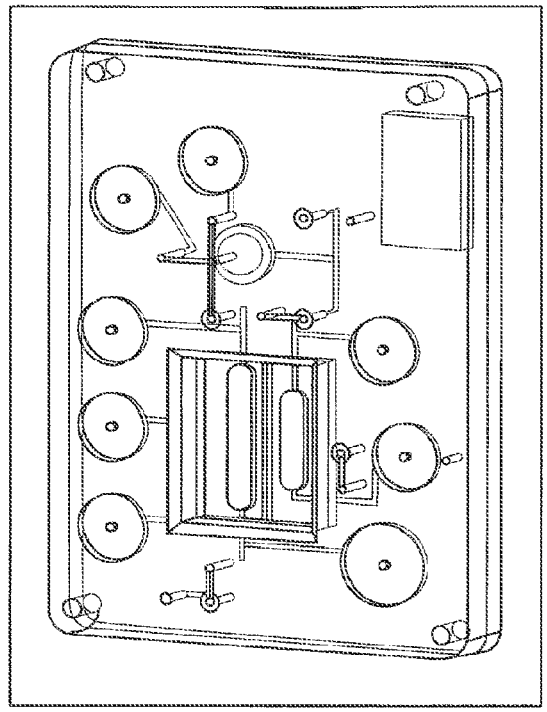
FIG. 12 depicts a cassette according to the instant invention that is suitable for nucleic acid analysis.
Figure 12B:
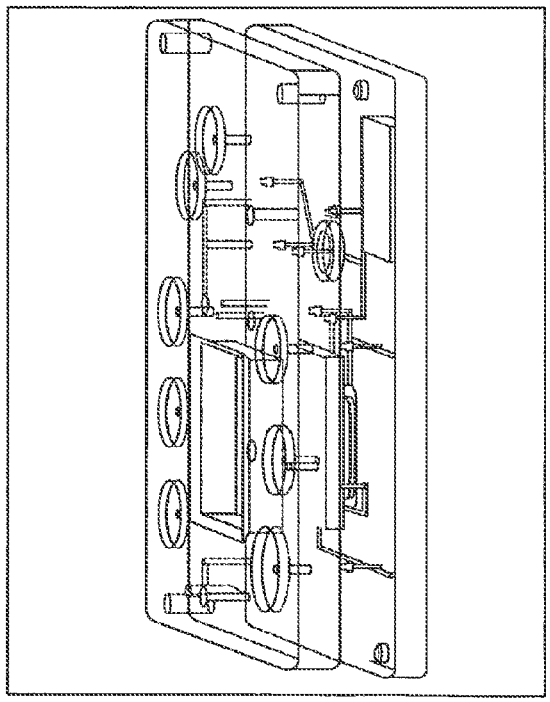

FIG. 12 depicts schematically the two parts of a cassette for the processing of nucleic acids. The depicted cassette meters a sample; lyses cells or viruses, isolates, concentrates, and purifies nucleic acids on a solid support; elutes the nucleic acids into a PCR chamber; and performs amplification of the eluted nucleic acids. FIG. 12a and FIG. 12b depict, respectively, a first and second components as separated and as mated together. The first component includes several depressions, which depressions may be capped to form blister-type fluid reservoirs.

FIG. 13 depicts an embodiment of the claimed invention of FIG. 12 suitable for application to PCR-based assays. FIG. 13a illustrates a first component that includes several blister reservoirs that contain reagents used for PCR reactions, including buffer, lysing reagent, and a binding reagent. The first component also includes a receiving chamber, which may be used to receive or hold any fluids that may participate or arise out of a given reaction, including waste fluids or even reaction products. FIG. 13b shows a second component including a silica membrane for trapping nucleic acids that may be liberated from lysed cells, a metering chamber used to control the volume of reagent or sample that may be transported from one fluidic element to another. FIG. 13c shows the two parts mated to form a cassette. FIG. 13d shows the cassette inside the actuator.

Figure 13C:
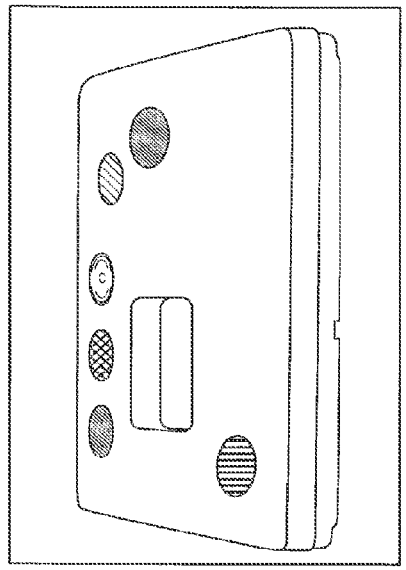
FIG. 13 illustrates the cassette shown in schematic view in FIG. 12.
Figure 13D:
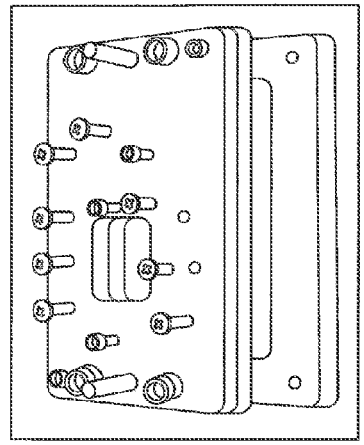
Figure 13A:
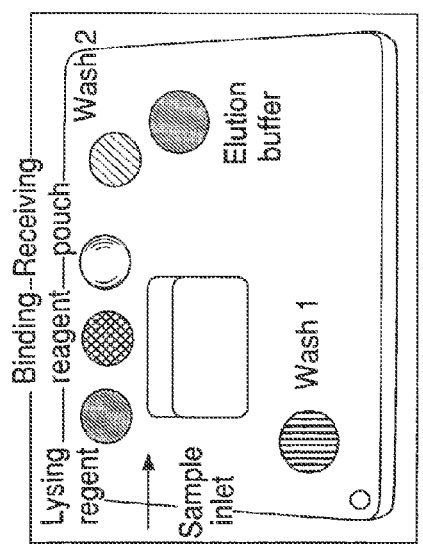
Figure 13B:
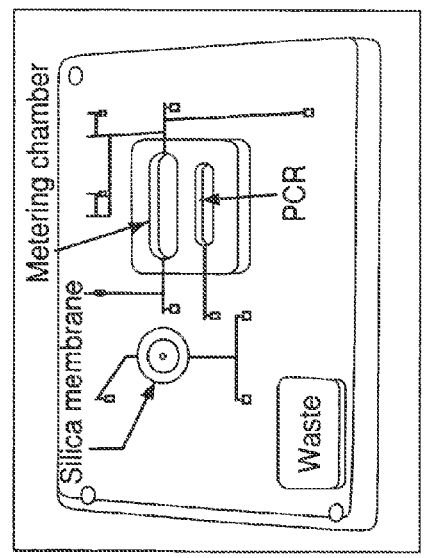

A metering chamber may be utilized by allowing a chamber of desired volume to fill and then closing valves at both ends of the chamber to prevent additional inflow. FIG. 13d illustrates an actuator capable of accommodating the component shown in FIG. 13a. Other useful configurations of valves and chambers will be apparent to those having ordinary skill in the art.

Figure 3:
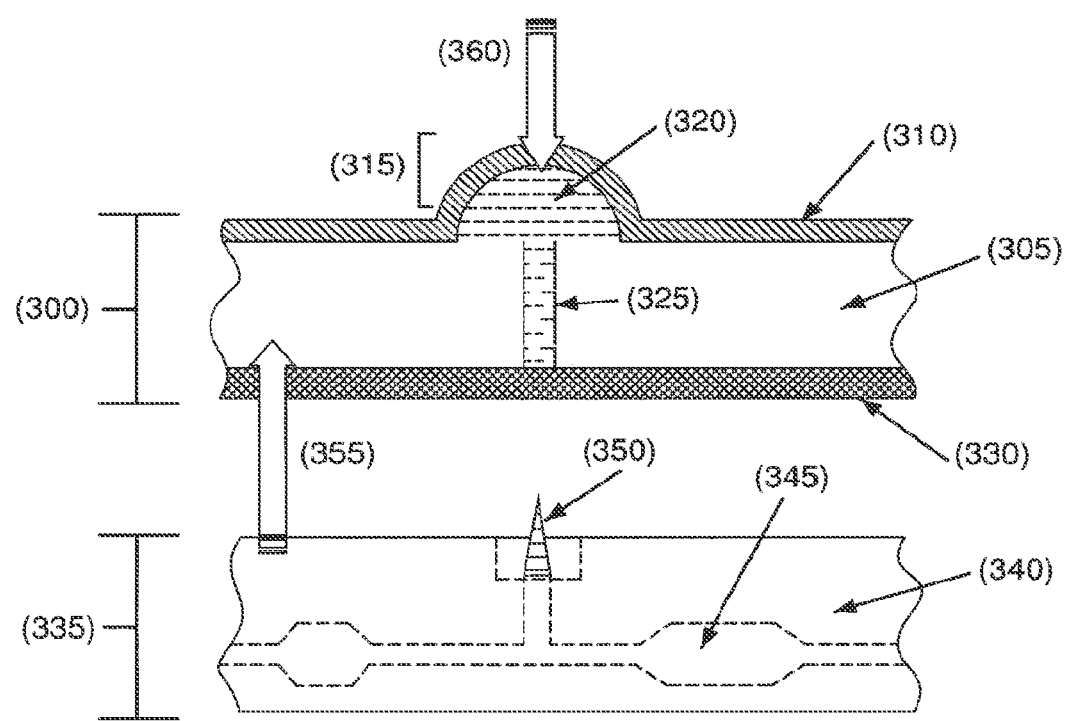
FIG. 3 depicts a cassette having a component with a fluid reservoir and a component having a hollow connector.

FIG. 3 depicts an exemplary embodiment of the disclosed systems. In the figure, a first component (300) includes a substrate (305) and a flexible layer (310) attached to one side of the substrate. The flexible layer is shaped to form one or more pouches (315) that contain fluids (320). An aperture (325) is formed in the substrate to fluidically couple the contents of the pouches to the opposing side of the substrate, where a material (330) is attached to that opposing side of the substrate and serves as a seal. The embodiment further includes a second component (335), which second component includes a substrate (340), that includes a microfluidic channel or circuit (345). The substrate of the second component also includes a hollow lance-type connector (350) that penetrates the seal material (330) to fluidically couple an aperture (325) to the microfluidic channel or circuit (345).

The first component (300) and second component (335) are preferably aligned and mated by application of a clamping force (355). The components, however, may also be mated by tabs, grooves, prongs, slots, and the like that are fabricated in one or both of the components, where the tabs, slots, and grooves are constructed so as to place the components into a particular alignment. The pouch (315) can be depressed by application of an external force (360) to propel a liquid (320) contained in the pouch (315) into the microfluidic circuit (345).

In some embodiments, not shown, the sealant layer is removed from the first component and the two components are mated together. Such embodiments may include one or more connectors; in some configurations, the sealant layer is removed and the components are mated together such that fluidic elements residing on the components are abutted together so as to place them into fluid communication without a connector.

Figure 4:
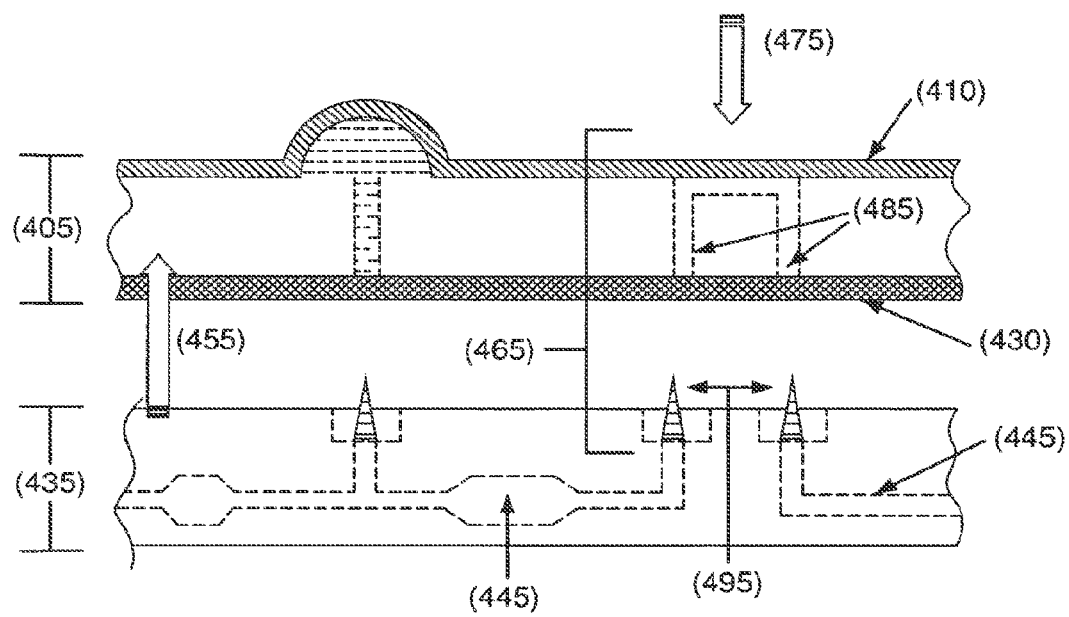
FIG. 4 depicts a cassette having a first substrate that includes a valve.

In another embodiment, FIG. 4, a valve realized in the first component (465) having a fluid channel (405) that is actuated by depressing flexible layer (410) with an applied force (475), and wherein said fluid channel is fluidically coupled to the microfluidic circuit (445) of the second component through apertures (485) and wherein lances (495) penetrate the frangible sealing layer (430) upon application of an external clamping force (475).

Figure 5:
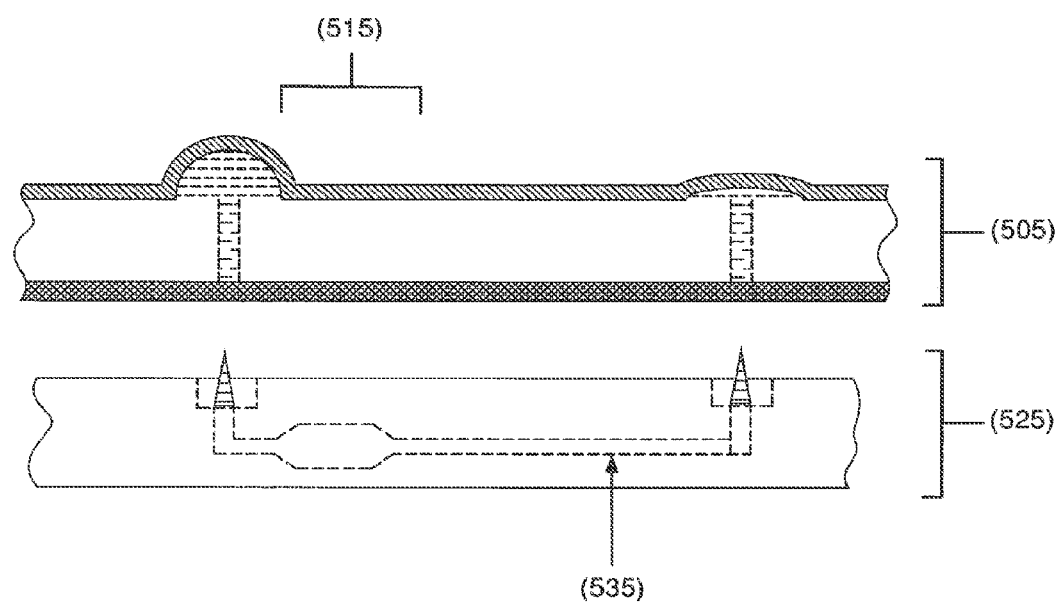
FIG. 5 depicts a cassette having two fluid reservoirs in fluid communication with each other and being capable of effecting mixing when the reservoirs are reciprocally depressed.

In another embodiment, FIG. 5, two pouches (515) formed on the first component (505) are fluidically coupled by a fluidic pathway (535) of the microfluidic circuit in the second component. In this embodiment, a first pouch is initially filled with fluid and a second pouch is initially empty, and a force applied alternatively between the two pouches induces reciprocating flow of liquid between the two pouches such that the mixing of the contents of the microfluidic pathway is enhanced.

Figure 6:
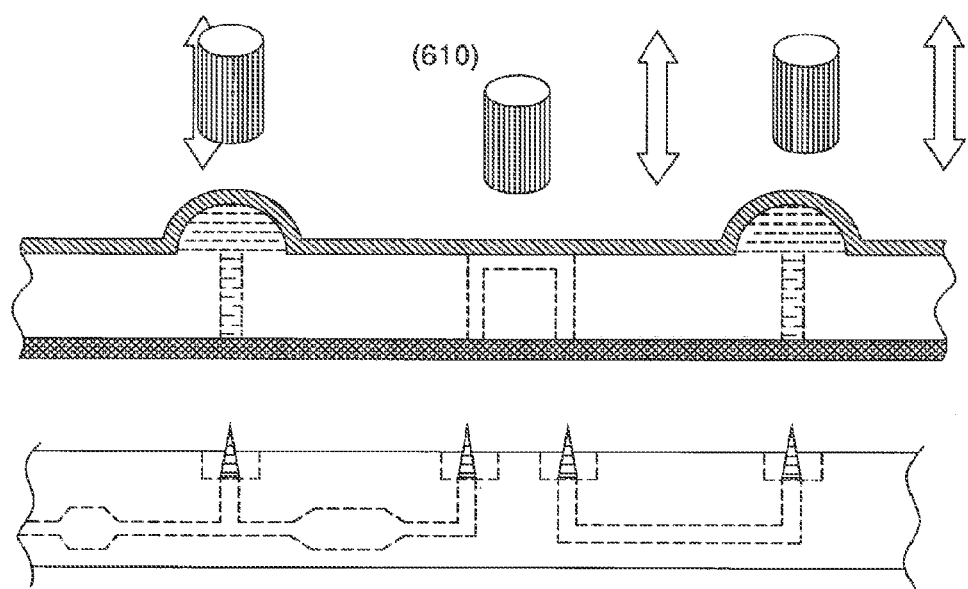
FIG. 6 depicts a cassette having multiple reservoirs in fluid communication with each other and being capable of effecting valving and mixing when the reservoirs are reciprocally depressed.

In a further embodiment, shown in FIG. 6, the devices shown in FIG. 3, FIG. 4, and FIG. 5 have pouches and valves actuated by the motion of shafts or plungers (600).

In another aspect, the claimed invention provides sample processing systems. Such systems include a component comprising at least one fluidic element sealed by a deformable sealing layer; and a moveable actuator residing proximate to the component. At least a portion of the actuator is capable of motion relative to the component, and the actuator suitably includes one or more actuator portions capable of actuating at least one fluidic element and also being arranged such that movement of the actuator effects a prescribed sequence of actuations. The actuations may be of the deformable sealing layer, or of one or more fluidic elements, or both. Movement of the actuator is suitably capable of effecting fluid motion within at least a portion of the component.

The claimed systems also preferably include an analysis device, which devices are described elsewhere herein. The systems also include a sample inlet, and, in some embodiments, a vent, which vent may be used as an outlet for excess or waste fluids or as an air outlet to facilitate the movement of fluid within the channels of the system.

An actuator portion suitably includes a protrusion, a ridge, a groove, an extension, an eccentricity, a depression, a ramp, a cam, or any combination thereof.

Components suitable for inclusion in the claimed processing system preferably include a fluidic element sealed by a deformable layer, which are described elsewhere herein. As a non-limiting example, a component may include one or more fluid reservoirs disposed on a substrate as in FIG. 2. The component may include one or more substrates the substrates including fluidic elements and being in fluid communication with one another as required by the needs of the user. The fluid processing systems described elsewhere herein are considered especially suitable components for the claimed systems. Preferably, a given component has one or more fluidic elements—described elsewhere herein—that are in fluidic communication with one another or are even in fluidic communication with one or more fluidic elements of a second component.

At least a portion of the actuator suitably contacts at least a portion of the component. In such embodiments, the actuator may directly exert a force on a fluidic element of the component. As an example, an actuator that includes one or more ridges is oriented such that rotation of the actuator brings one or more ridges into contact with a membrane-capped blister reservoir on the component. The contact of the ridge against the reservoir membrane then depresses the reservoir so as to force fluid out of the reservoir.

Figure 21:
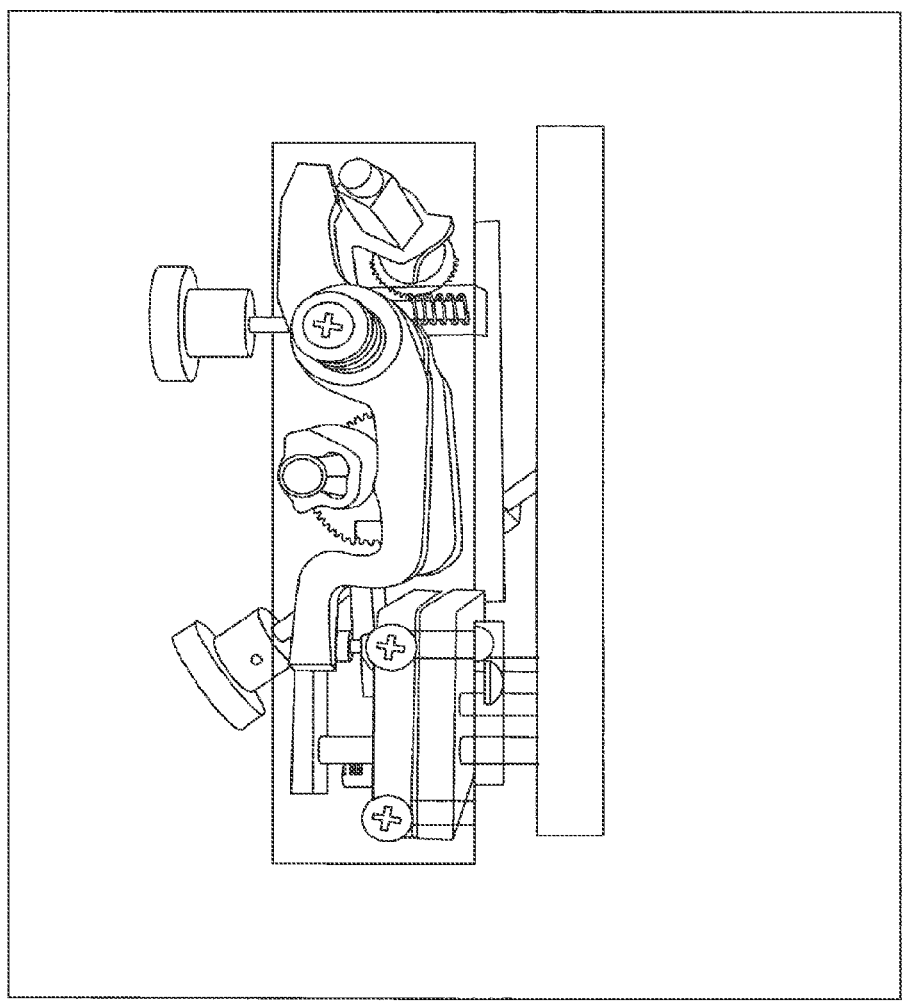
FIG. 21 illustrates an alternate view of a claimed device having eccentric camshafts capable of actuating hinged members.

In other embodiments, the system includes one or more hinged members residing proximate to the component, which members are preferably capable of being actuated by at least a portion of the actuator. One such arrangement is shown in FIG. 21, in which eccentricities disposed along the camshaft, upon rotation of the camshaft, are brought into contact with the hinged members residing proximate to the camshaft and actuate the hinged members.

Figure 23:
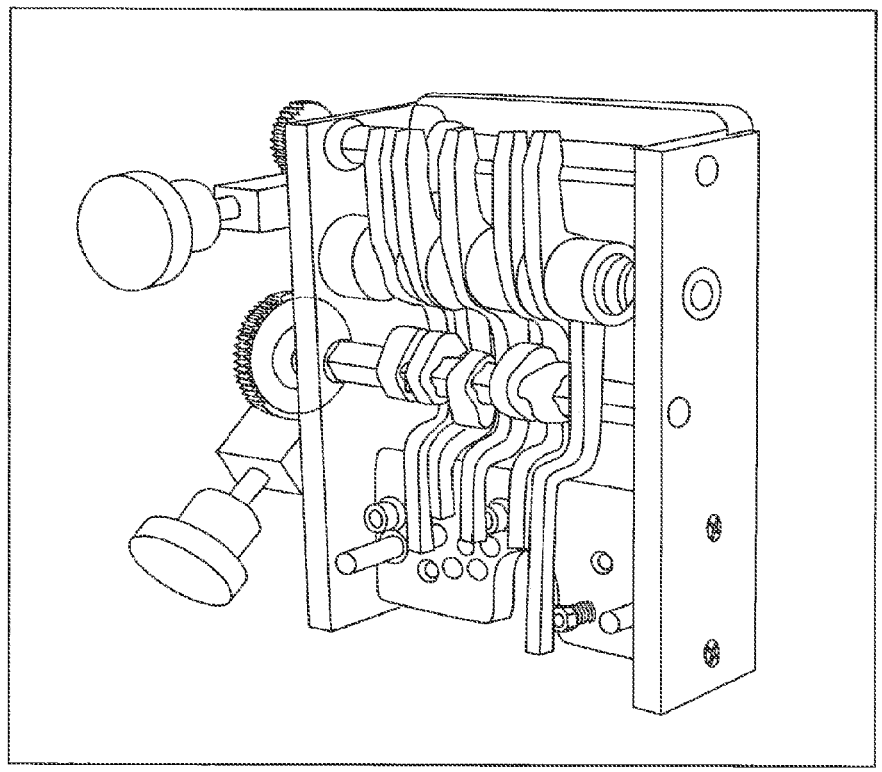
FIG. 23 illustrates a claimed device having multiple, eccentric camshafts capable of actuating proximate, hinged members.

An alternative view of such an embodiment is shown in FIG. 23, wherein a camshaft having several projections or eccentricities is located proximate to several hinged members in order that rotation of the camshaft brings the eccentricities into contact with the hinged members so as to actuate them. Accordingly—and as will be apparent to those having ordinary skill in the art—the arrangement of the hinged members and any eccentricities along the camshaft will give rise to a prescheduled sequence of actuations of the hinged members according to the eccentricities of the camshaft.

In some embodiments, a hinged member is capable of actuating one or more fluidic elements. In such embodiments, the rotation of the actuator actuates the hinged member so as to bring a portion of the hinged member into contact with a fluidic element of the component.

As a non-limiting example, an eccentric camshaft is rotated such that the eccentricity actuates a hinged member, which in turn depresses a blister reservoir and forces fluid out of the reservoir into a channel connected to the reservoir. As the camshaft rotates, a second eccentricity rotates into contact with a second, different hinged member, which in turn actuates a second fluid reservoir in fluid communication with the first reservoir, thus effecting reciprocal motion of the fluid previously forced from the first reservoir. As the camshaft is further rotated, a third eccentricity actuates a third hinged member that opens a valve while the first eccentricity presses on the first fluid reservoir, thus forcing the fluid past the now-opened valve into a particular region of the system, which region may be a reactor, a detector, a channel, and the like.

The system may also include a heater, which heater may be turned on and off by the movement of one or more hinged member. As the user of ordinary skill in the art will appreciate, the claimed system is adaptable to many different sequences of fluid motions and processes, which sequences may be dictated by the arrangement of physical features on the actuator and of fluidic elements on the component substrate.

Figure 14A:
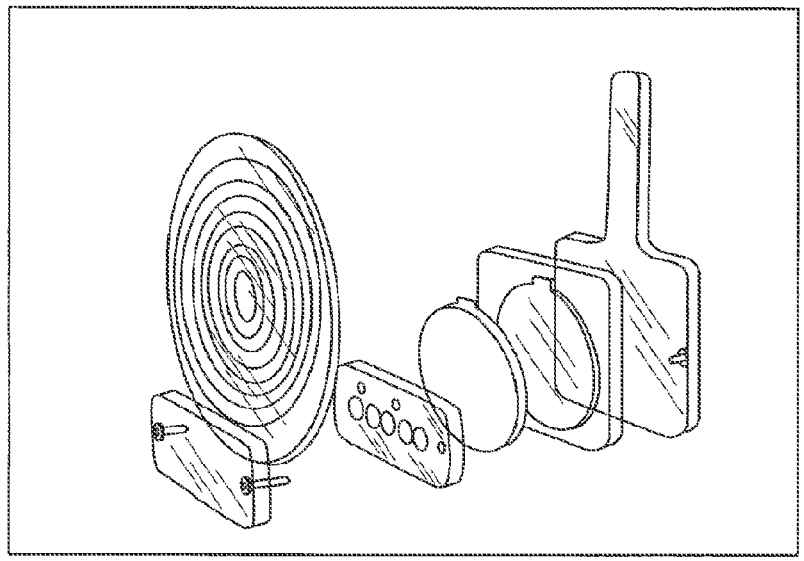
FIG. 14a illustrates an embodiment of the diagnostic device of the instant invention, comprising a cassette positioned within a slider disc assembly.
Figure 14B:
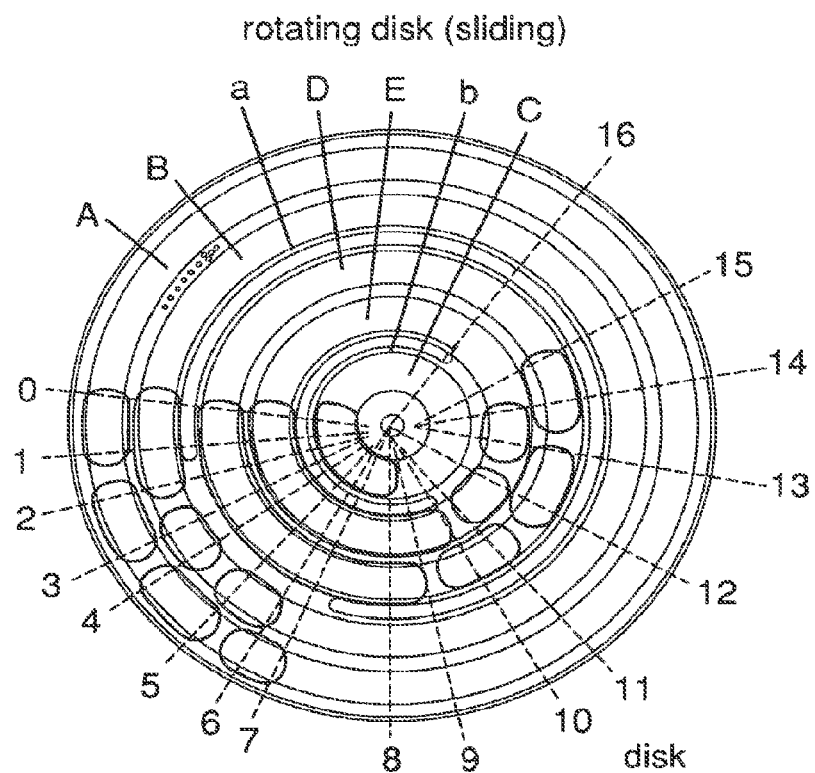
FIG. 14b depicts a sample arrangement of surface features on a slider disc so as to enable a prescheduled sequence of actuations.

While the described embodiments focus on camshaft actuators, the motion of the actuator may be linear motion, rotational motion, or any combination thereof. In some embodiments, the actuator may have at least one surface residing substantially parallel to the component, such as a disc or slider. Such an embodiment is shown in FIG. 14a, which illustrates a slider disc adjacent to a pouched cassette of reagents and fluids. As shown in FIG. 14b, the slider disc may have ridges and depressions such that rotational motion of the disc relative to the pouch in turn actuates various elements—pouches, valves, vents, and the like—are fabricated on the cassette.

Figure 15:
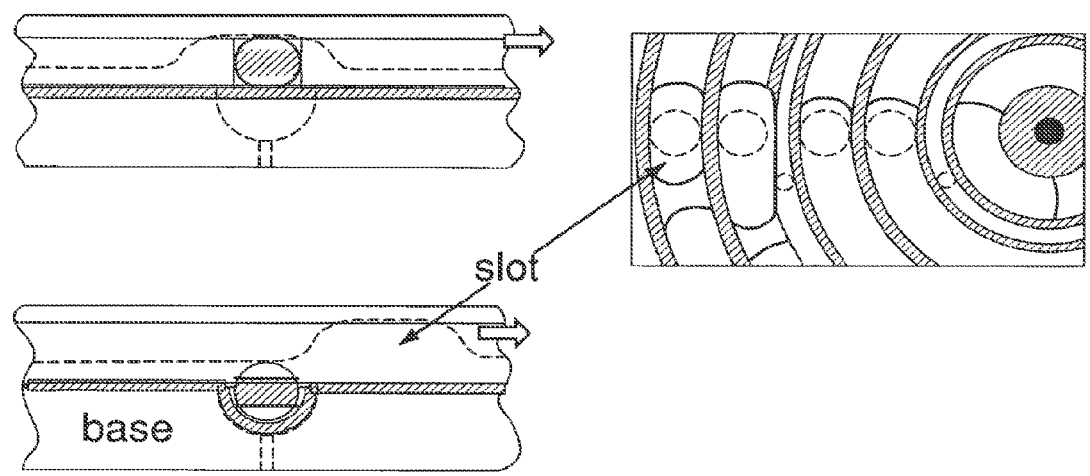
FIG. 15 depicts a ball positioned within a slot so as to exert a force on a base or pouch residing within the device of FIG. 14b.

FIG. 15 depicts an additional embodiment of the disc-based system described above. In this additional embodiment, a ball is positioned between the slider disc and the pouched cassette. As the disc is rotated, ridges and protrusions of the disc contact the ball, which in turn presses the ball into a deformable membrane residing above a reservoir or other element on the pouched cassette, which forces fluid out of the reservoir or element. In some embodiments, an object having a piercer or point is positioned between the slider disc and the pouched cassette such that rotational motion of the disc results in the object piercing the membrane so as to liberate a fluid or, in other embodiments, to create a vent hole.

In some embodiments, the system includes a plunger positioned so as to actuate a fluidic element. Such plungers may be actuated by the physical features of the actuator or by hinged members that are themselves actuated by the motion of the actuator. The plungers are suitably capable of reversible motion and such that they may be cycled between up and down positions.

Plungers may have a latch, a spring-loaded bayonet-type coupling, or other mechanism capable of maintaining the plunger in an up or down position until the mechanism is actuated. In other embodiments, however, the plungers are irreversibly moved. In these embodiments, actuation of a plunger against a membrane results in permanent depression of the membrane, which permanent depression may act as a valve by closing off a channel or reservoir that resides beneath the membrane.

Figure 18A:
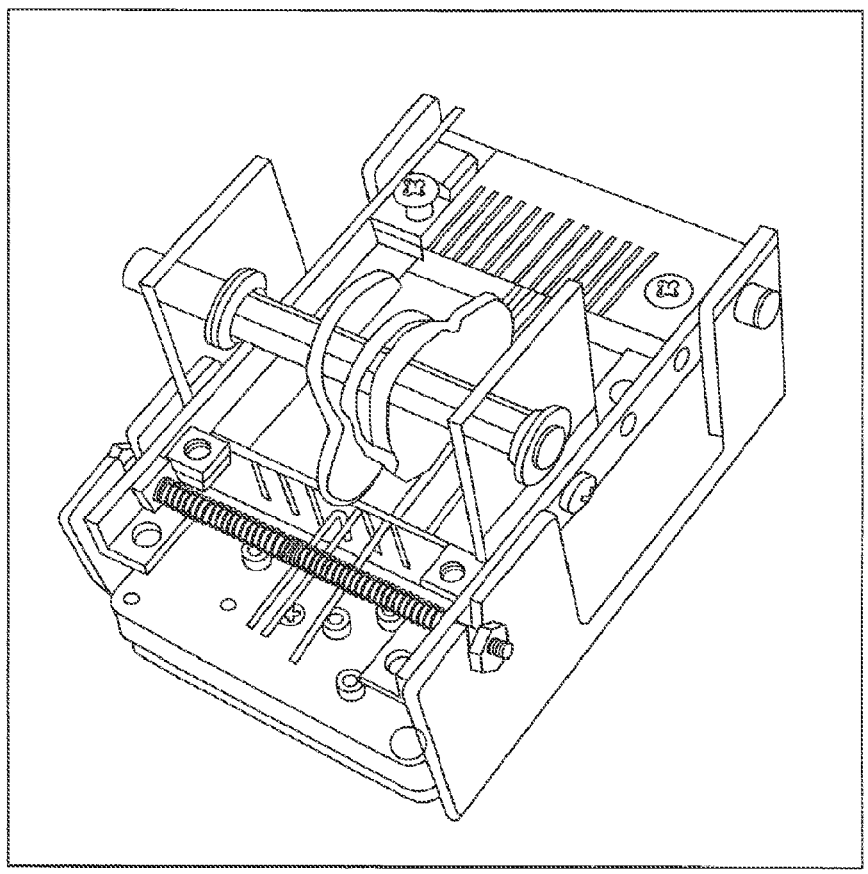
FIG. 18a illustrates an embodiment of the instant invention comprising a camshaft and multiple hinged members capable of being actuated by the camshaft.
Figure 18B:
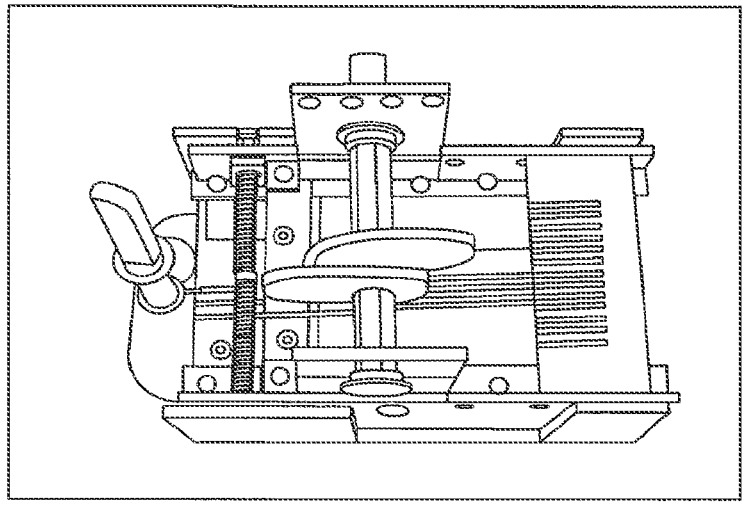

FIG. 18a illustrates one embodiment of the claimed invention having a camshaft that actuates hinged members. The eccentricities located toward the middle of the camshaft are capable, depending on the degree of camshaft rotation, of contacting the hinged members located below the eccentricities, which in turn presses on the eccentricities. The depressed eccentricities may then press downward on a plunger or pin, shown in FIG. 18b.

FIG. 18c illustrates an actuator having a camshaft in contact with several hinged members. A power source turns a driveshaft in contact with a camshaft so as to rotate the camshaft and bring the eccentricities located on the camshaft into contact with the hinged members also present on the actuator, shown from a different perspective in FIG. 18d. FIG. 18e illustrates an actuator having a slot into which a cassette is inserted. As described elsewhere herein, such a configuration enables a modular system in which different cassettes containing different reagents specific to a particular reaction are compatible with a standardized actuator. Such modular systems enable a broad variety of reactions and assays to be performed by using pre-prepared reagent modules.

Figure 18F:
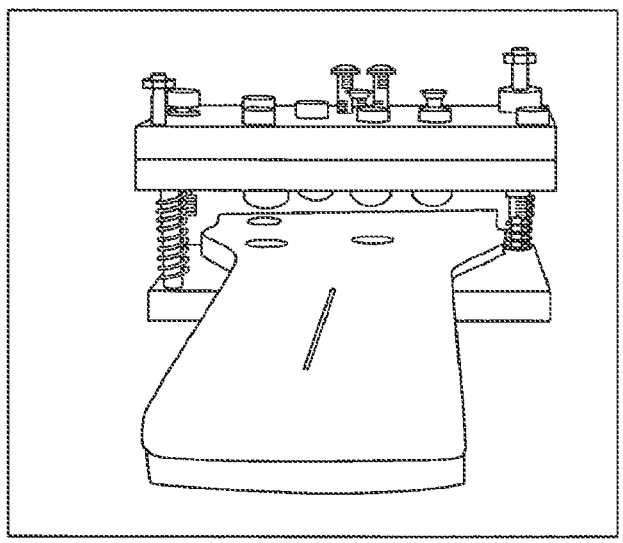

An additional, non-limiting plunger embodiment is shown in FIG. 18f. In that embodiment, plungers are integrated into the processing system and are oriented perpendicular to a cassette having several fluid reservoir blisters. Thus oriented, the plungers—when actuated—then depress the fluid blisters below, forcing fluid from the blisters into fluidic elements disposed within the system.

Figure 19:
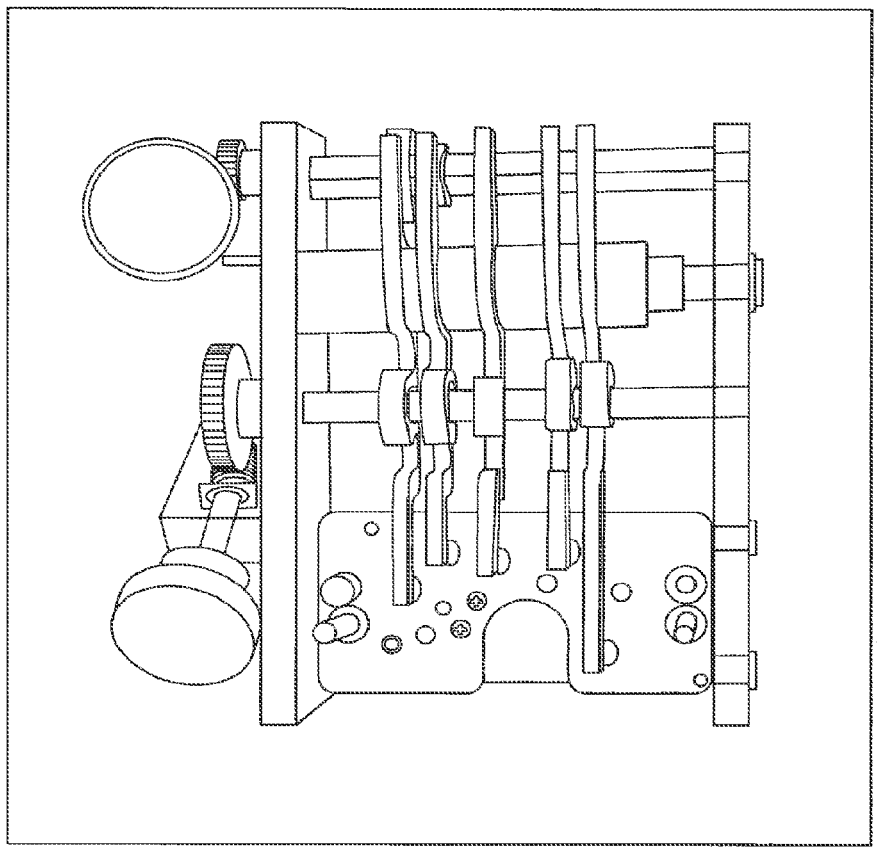
FIG. 19 illustrates an embodiment of the claimed device having an eccentric camshaft capable of actuating hinged members.
Figure 20:
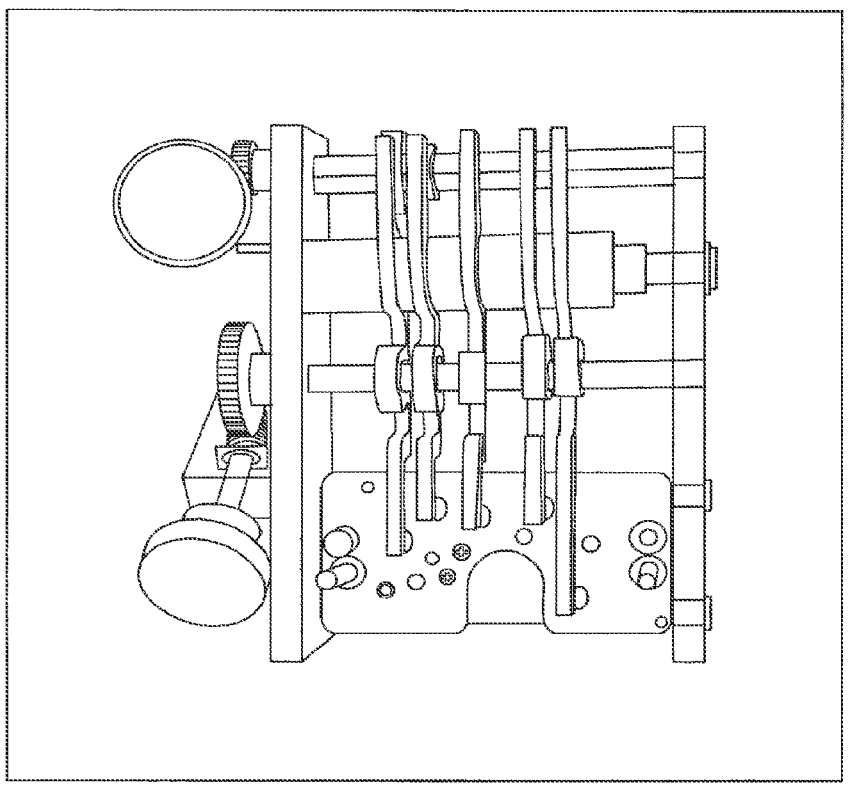
FIG. 20 illustrates an embodiment of the claimed device having an eccentric camshaft capable of actuating hinged members.

An alternative plunger embodiment is shown in FIG. 19 and FIG. 20. In that embodiment, several hinged members are positioned above several plungers. As the camshaft of the embodiment is rotated, the eccentricities of the camshaft contact and actuate the hinged members, which actuated members in turn depress the plungers located below.

Figure 22:
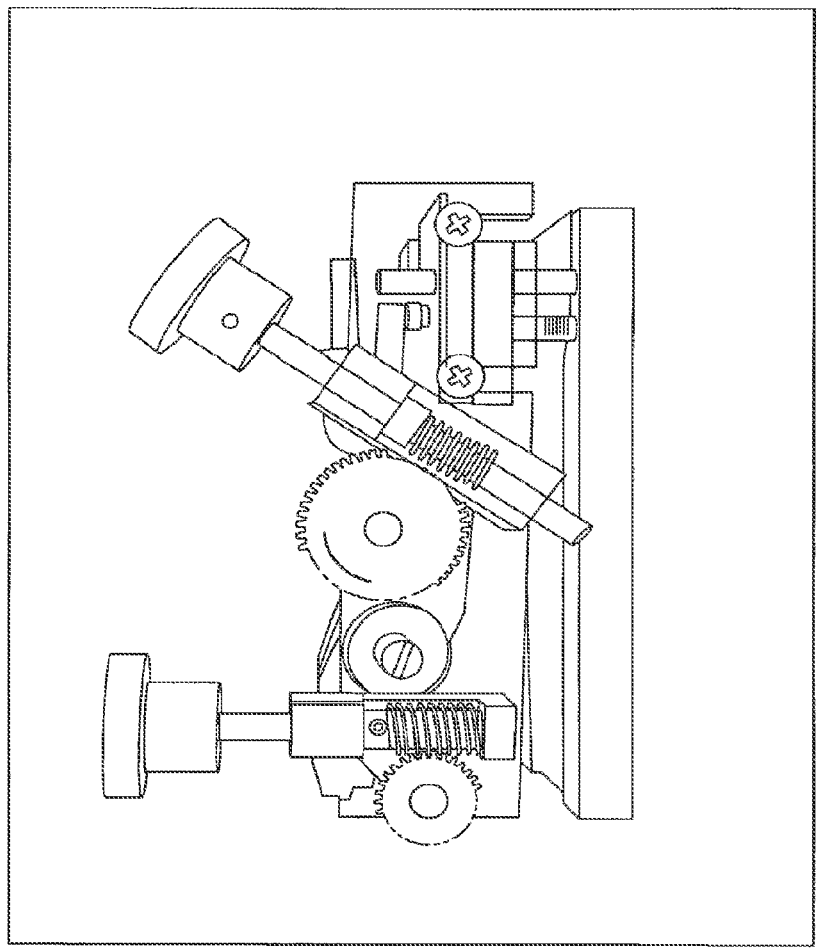
FIG. 22 illustrates a claimed device having eccentric camshafts capable of actuating hinged members.

FIG. 21 depicts a further embodiment of the claimed system. In this embodiment, several hinged members are shown positioned above plungers, which plungers are then positioned above one or more fluidic element—such as reservoirs or valves—in a cassette. The hinged members are themselves actuated by two separate camshafts, also shown in FIG. 22. Accordingly, by employing multiple camshafts, the disclosed system enables simultaneous actuation of multiple hinged members.

In some embodiments, the cassette and actuator assembly are constructed such that the cassette is removably insertable into the actuator assembly. Such an embodiment is shown in FIG. 18f, FIG. 18g, and FIG. 21, all of which depict an actuator assembly having a slot or opening capable of accommodating an inserted cassette.

Such embodiments make possible the construction of a modular and flexible system for fluid processing where different cassettes may be inserted into an actuator system. In one non-limiting example, different cassettes containing different fluid reagents suitable for different analyses or assays can be prepared. Depending on the user's needs, the proper pre-loaded cassette is selected from a number of pre-loaded cassettes and inserted into the actuator assembly for sample introduction and processing. As will be apparent to the user having ordinary skill in the art that a wide range of cassette configurations is possible, and actuators and complementary cassettes may be constructed so as to perform a broad range of reactions and assays.

Actuators may be motivated in a number of ways. In one embodiment, the actuator is manually motivated, wherein the user turns a camshaft, rotates a disc, or slides a slider bar. Such embodiments are considered especially suitable for environments or situations where electrical power may not be easily available. Movement of the actuator may also be accomplished by electric motor, solenoid, pneumatic drive, magnetically, or by any combination thereof. Users of ordinary skill in the art will readily identify other suitable methods for motivating an actuator.

The movement of the actuator may be governed by a controller. Governance of the actuator's movement may be of particular interest where the user seeks to effect a relatively complex sequence of chemical, biochemical, or biomolecular reactions, in which sequence certain reactions are to proceed for a specific period of time. Such control may be accomplished by computer controllers, gears, or even by spring-loaded mechanisms that release stored energy over time and actuate different parts of a system as that energy is released.

The systems also, in some embodiments, include a heater, a cooler, or both. The heater and cooler may give rise to a prescribed set of temperature changes, and, as described elsewhere herein, may be actuated by movement of the actuator. The heater and cooler may also be actuated by the user, and may reside within the processing system or external to the system.

The use of a heater is illustrated by a system used to effect a PCR reaction on a given sample. As is known in the art, as the PCR reaction progresses, the reaction is enhanced by the addition of heat. As applied to the claimed system, the actuator may turn on one or more heaters at the appropriate intervals in a given PCR reaction so as to optimize the reaction's progress. Where a strongly exothermic reaction is effected, the system may be arranged such that movement of the actuator turns on one or more coolers so as to moderate the reaction temperature and prevent reaction runaway.

Without being bound to any particular theory of operation or invention scope, the claimed system is, in some embodiments, capable of effecting and controlling a sequence of reactions through the user-controlled motion of a single actuator. In such embodiments, the movement of the actuator moves fluids, opens valves, introduces reagents into a sample, mixes the sample and reagents, and transports the reaction products to a detector or analysis device, without the need for user intervention beyond activating the actuator.

Figure 24A:
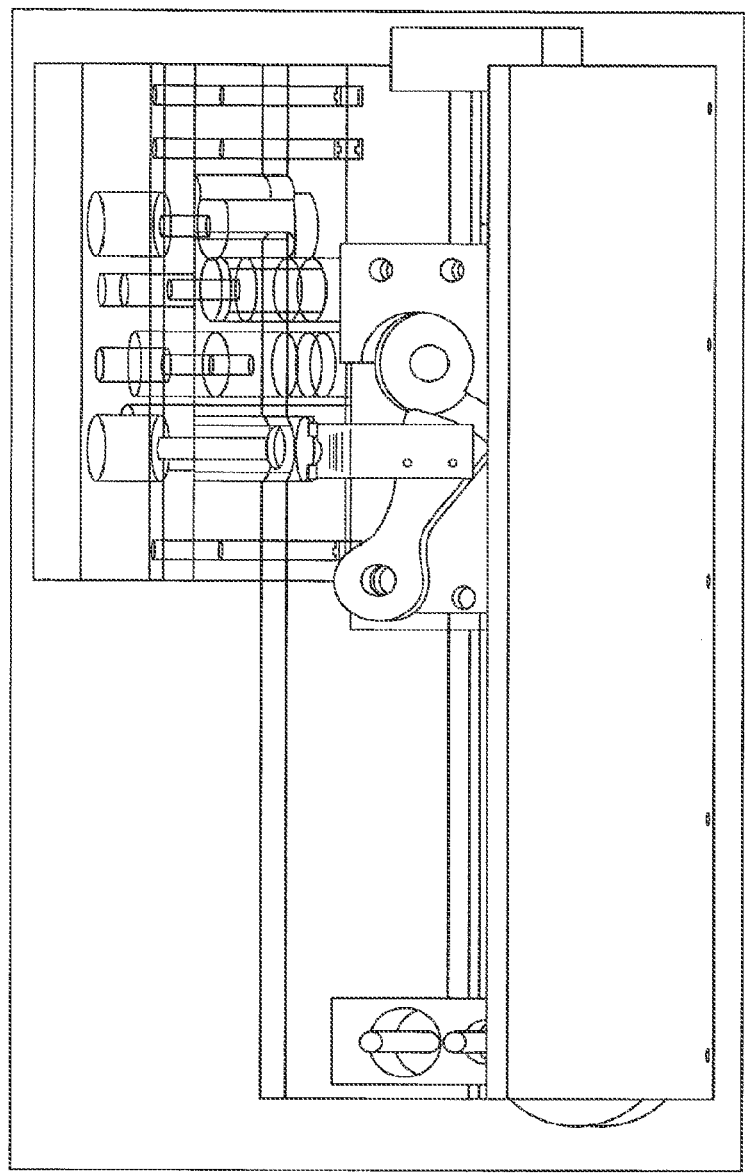
FIG. 24a depicts a claimed device having an x-y translatable actuator.
Figure 24B:
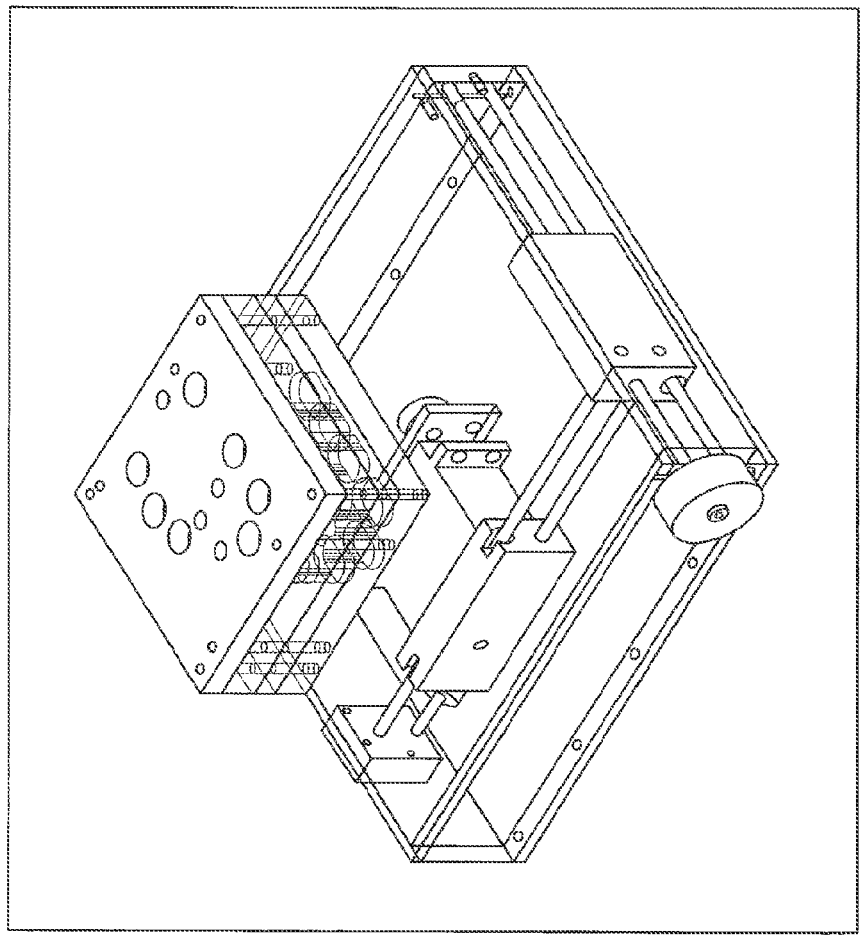
FIG. 24b depicts a claimed device having an x-y translatable actuator.

In one embodiment, the actuator comprises a piston, plunger, or other device capable of applying pressure to a discrete area, mounted on a stage capable of movement in the x-y plane. An exemplary device is shown in FIG. 24a and FIG. 24b, where a piston actuator is mounted on an x-y stage, which stage is disposed under a cassette. The piston may be moved to the x-y coordinates of a particular fluidic element, where the piston is actuated, thus pressing on the fluidic element. In the case of a fluid reservoir, the piston depresses the membrane capping the reservoir, which in turn forces fluid out of the reservoir. The actuator may be moved according to a pre-programmed schedule of locations, at which locations the actuator actuates a fluidic element at that location. A given system may have two or more actuators, thus enabling simultaneous actuation of multiple fluidic elements residing on a cassette within the system.

Further disclosed are methods for analyzing a sample, which sample may include biological materials, water supplies, food, beverages, and the like. The disclosed methods first include placing the sample into a component comprising two or more fluidic elements in fluid communication with one another, with one or more fluidic elements of the component being surmounted by a deformable layer. Suitable components are described elsewhere herein.

The methods further include controllably subjecting at least a portion of the sample to one or more processing steps that are effected by the movement of an actuator relative to the first substrate, where the actuator includes one or more physical features arranged so as to effect a predetermined schedule of processing steps when the actuator is moved relative to the component. One—or more—of the processing steps includes transport of the sample from one fluidic element to another. The sample is then analyzed for the presence of one or more analytes.

Suitable fluidic elements and components are described elsewhere herein. Samples may be placed or introduced into a component by pipetting, dispensing, spraying, and the like. In one embodiment, a sample is pipetted into a fluidic element by the user.

After being placed into a component or fluidic element, a sample is subjected to one or more processing steps. Such steps include transporting, altering temperature, mixing, reciprocal fluid motion, adsorbing, absorbing, dyeing, tagging, fluorescent labeling, radiolabeling, magnetic labeling, separating, reacting, detecting, polymerizing, amplifying, separating, or any combination thereof. The processing steps suitable for a given objective will be known to users of ordinary skill in the art, and can include placing two or more fluidic elements in fluid communication with one another.

As one example, the processing steps for effecting a PCR reaction may include introducing a cell sample suspension into a fluid reservoir surmounted by a flexible membrane and depressing the membrane to transport the sample suspension into a chamber where one or more lysing reagents are introduced. Following the lysing, the resultant nucleic acid is concentrated and then amplified by the introduction of primers, dyes, and additional nucleic acids. The resultant products are then transported to a detector station, such as a capture zone in which product is selectively captured and visualized.

The disclosed methods contemplate that one or more processing steps are effected by compressing at least a portion of the deformable layer that surmounts the one or more fluidic elements. As described elsewhere, such deformation can force fluid out of the reservoir residing beneath the layer or membrane. In some embodiments, the processing step includes exposing the sample to a reagent, which exposure can be effected by the actuator depressing a valve or breaching a barrier so as to liberate stored reagent and to allow that reagent to mix with the sample.

Actuators suitable for the claimed methods are described elsewhere herein. In the disclosed methods, the sequence of processing steps is effected by the motion of the actuator relative to a component such that one or more physical features of the actuator contact the component to actuate one or more fluidic elements of the component in a prescribed schedule that accords with the arrangement of physical features on the actuator. Suitable physical features include, inter alia, bumps, ridges, grooves, ramps, cams, and the like. As the actuator moves relative to the component, one or more of the physical features exerts a force on a fluidic element—such as a blister reservoir—of the component, so as to effect fluid flow. A feature of the actuator may also open or close a valve within the component. In some embodiments, Processing steps may also be accomplished by actuating a process module residing on or within the component or external to the component. These actuations may be accomplished by the actuator contacting a switch to turn the module on or off, or by the actuator moving a lever that in turn switches the module on or off As an example, an actuator may be used to turn a heater on—or off—at a particular stage of a reaction or assay so as to provide heating—or cooling—at the optimal time. The user of ordinary skill in the art will appreciate the numerous ways in which an actuator may activate—or deactivate—a given module.

The analysis aspect of the claimed methods comprises, in some embodiments, visualizing a target. Such visualizing may be accomplished by selectively labeling the target—which may be one or more products of a reaction performed on a sample—with a dye or tag and then visually inspecting the target for the label. As an example, DNA extracted from a cell sample is labeled with a fluorescent dye and then—when illuminated at the dye's excitation wavelength—inspected. Other analysis techniques include assaying for the product of a reaction between the sample and one or more chemical species.

The pouch system can also facilitate thermal cycling by moving a sample among fluidic elements that are maintained at different temperatures. As one example, a sample can be continuously transported between two reservoirs where each reservoir is maintained at a different temperature, as may be needed for an effective PCR reaction. Systems capable of performing a PCR reaction by metering a cell-containing sample, performing lysis, isolating nucleic acids, and amplifying the isolated nucleic acids are considered especially suitable. One method of doing so is set forth in U.S. Application 61/012,667, "An Integrated PCR Reactor for Cell Lysis, Nucleic Acid Isolation and Purification, and Nucleic Acid Amplification Related Applications," filed on Dec. 10, 2007, the entirety of which is incorporated by reference herein.

NON-LIMITING EMBODIMENTS AND EXAMPLES

Described below are certain embodiments of the present invention for illustration purposes. Although these embodiments are representative of the invention, they do not also limit the scope invention.

Example 1

A cassette according to the present invention was prepared by using milling procedures, known to those having ordinary skill in the art, to form depressions in a polymeric substrate, which depressions were then capped by a flexible elastomeric membrane and filled with fluid and sealed to form blister reservoirs, as shown in FIG. 3. The cassette also included a lateral flow strip, suitable for immobilizing labeled target molecules.

Example 2

A cassette according to the present invention was constructed, which cassette included several fluid reservoirs and several membrane valves, as shown in FIGS. 7a-7d. The cassette also included a silicon microbead array, as shown in FIG. 9. The cassette was then mated to a custom-constructed lower substrate comprising multiple fluidic channels and hollow connectors, as shown in FIG. 9. A sample of a 125 nM IL-8 target was then introduced into the cassette-substrate assembly, as shown in FIG. 10, washed with a detection antibody solution and a labeling solution, which solution consisted of a 3 ug/mL biotinylated anti-IL-8 and 20 ug/mL streptavidin-AlexaFluor 488, and then and washed with buffer. All steps were performed by actuating the reservoirs and channels of the cassette with an actuator as depicted in FIG. 10.

Figure 11:
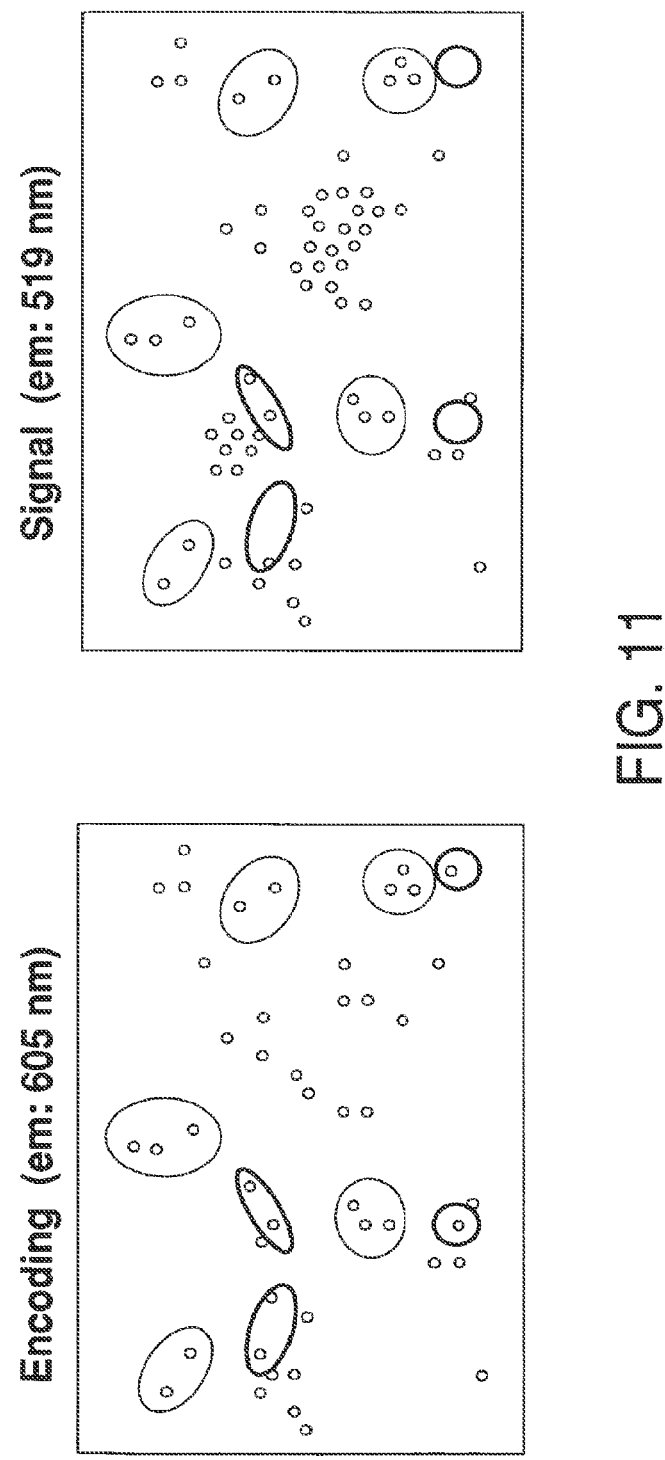
FIG. 11 depicts an image obtained from a bead array functionalized with anti IL-8 and anti-VEGF where only IL-8 is present in the sample.

The results of the antibody assay are shown in FIG. 11. FIG. 11 shows anti-IL8 and anti-VEGF beads, after incubation with the IL-8, that were illuminated by 605 nm wavelength light; both kinds of beads were visible. Upon illumination by 519 nm light, only those beads complementary to IL-8 fluoresced, thus demonstrating target capture.

Example 3

A cassette according to the present invention is prepared and mated to a substrate comprising several fluid conduits and a lateral flow strip. FIGS. 7a-7c illustrates such a cassette, in which figure separate fluid reservoirs and the lateral flow strip are shown. The cassette is then inserted into an actuator, as shown in FIG. 7d. FIG. 18g shows a cassette being inserted into an actuator comprising a camshaft and several hinged members capable of actuating individual or multiple hinged members such that the members contact different portions of the cassette so as to squeeze reservoirs and mix fluids within the cassette-substrate assembly. The cassette and substrate are adapted for nucleic acid amplification by PCR and subsequent testing of the PCR product.

In the nucleic acid-adapted cassette, a sample laden with cells, bacteria, or viruses—or a combination—is initially introduced to the device, where actuation of the camshaft transports the sample into the device and liberates fluid from one or more fluid reservoirs on the cassette so as to dilute the sample with buffer and mix the sample with lysing and binding reagents. The lysate is then transported to a silica membrane to which the nucleic acids adsorb. After a thorough washing, the nucleic acid is eluted and then mixed with PCR reagents and transported to a PCR chamber.

Figure 17:
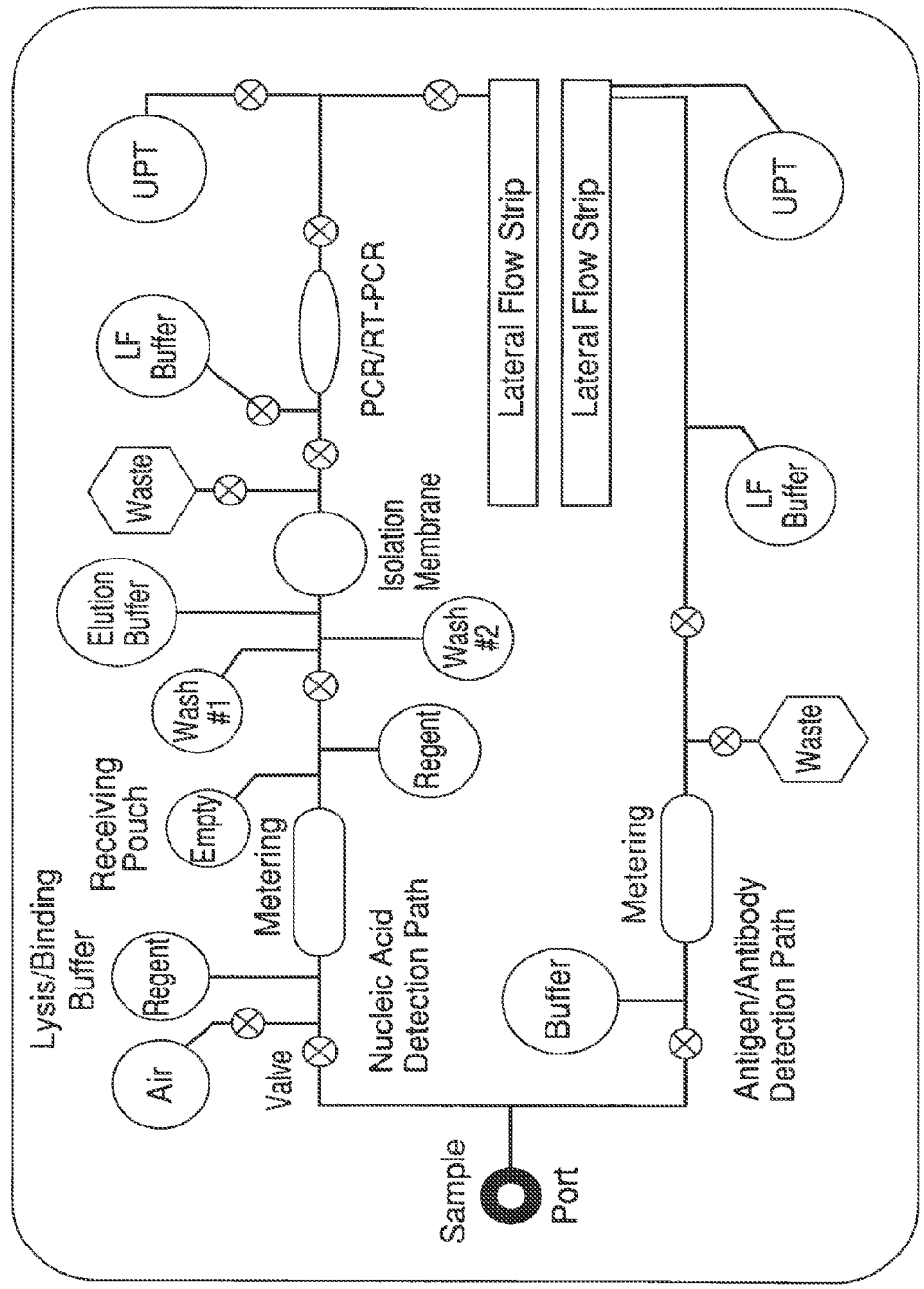
FIG. 17 depicts an exemplary sequence of steps for nucleic acid and protein processing as performed on a device or devices according to the claimed invention.

The temperature cycling of the PCR chamber is accomplished either with a stationary heater whose power is being controlled or by multiple, individual heaters that are brought into contact with the PCR reactor for desired time intervals. In the latter case, the movement of the camshaft actuates a cycling heater so as to enhance the progress of the PCR reaction. The movement of the camshaft is controlled so as to perform the optimum number of heating cycles for the optimum amount of time for the PCR reaction. The PCR product is then transported from the PCR chamber, labeled with a specific labeling species, and transported to the lateral flow strip, where the labeled PCR product may be visualized. A schematic overview of the process is shown in FIG. 17.

Example 4

A further embodiment of the claimed methods is shown in FIG. 10. A sample may be introduced into a system—as described elsewhere herein—by injection. By actuation of a valve and a fluidic reservoir by actuator, the sample is moved to a microarray contained within the system A detection label solution is transported from a reservoir into the system and across the array, again by action of an actuator. A buffer is then introduced into the system and flowed across the array, which buffer is flowed by the pneumatic effect of an actuator depressing a fluid reservoir. As shown in FIG. 10, the system includes an actuator comprising pins and screw-type members capable of actuating fluid reservoir pouches and valves. The pins and screw-type members may be actuated manually or by an actuator having physical features—such as ridges—complementary to the pins and screw-type members.

Example 5

Figure 16:
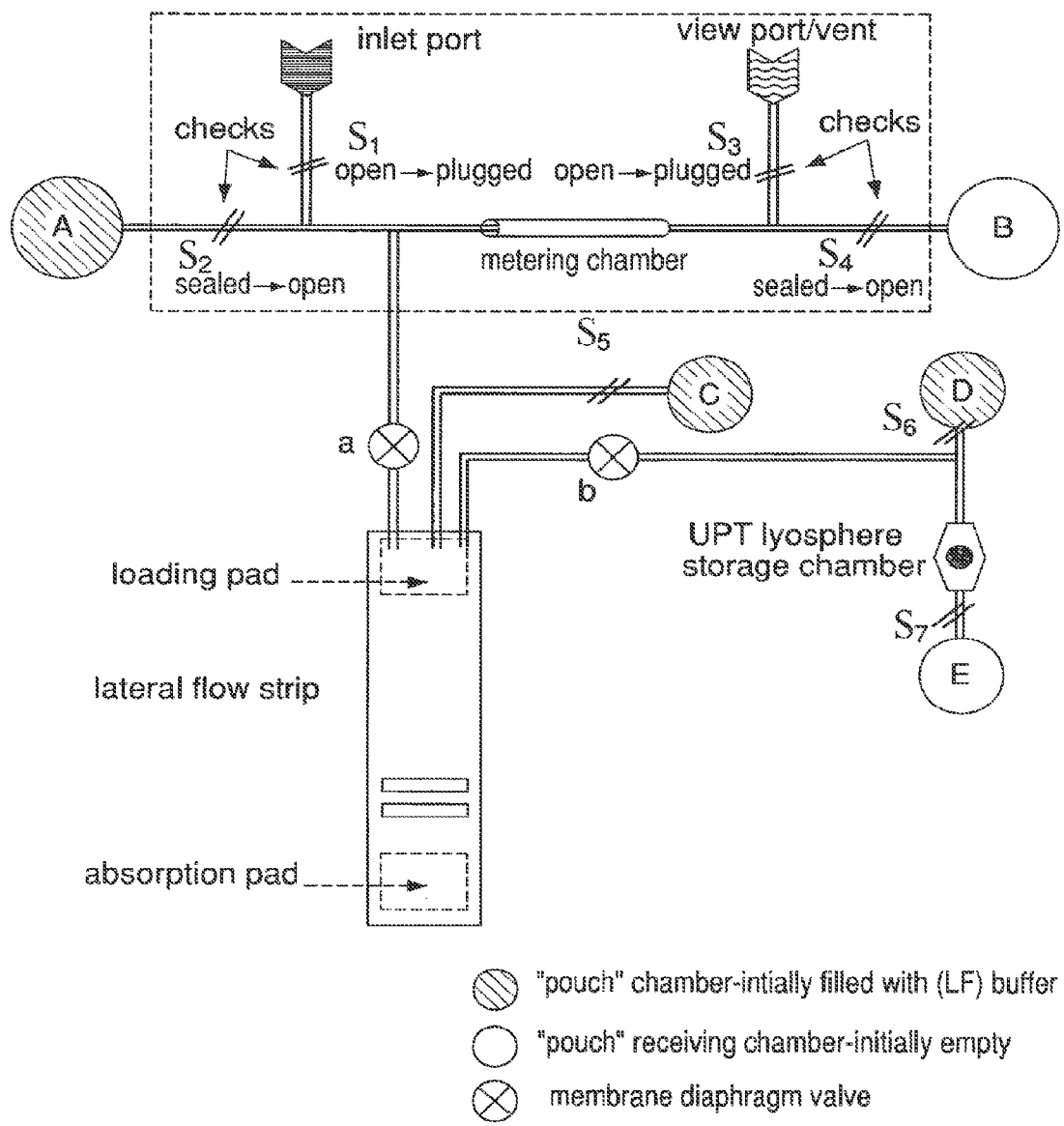
FIG. 16 depicts a sample arrangement of elements on a device of the claimed invention suitable for performing a lateral flow assay.

An exemplary, non-limiting reaction scheme is shown in FIG. 16. A sample may be introduced at the inlet port and admitted into the system by stop S1. Once admitted into the system, pouch A—containing a buffer—may be depressed, thus conveying the sample into the metering chamber. Reservoir B may be actuated in concert with stops S3 and S4 and the metering chamber so as to admit the desired amount of buffer into the system. Valve a may be opened to admit buffered sample to a lateral flow strip, where stop S5 may be opened to admit additional buffer from reservoir C when reservoir C is actuated. Stop S6 may be opened to admit buffer from reservoir D and UPT-lyosphere propelled by actuation of reservoir E, which materials are then admitted via valve b into the lateral flow strip. At the strip, the sample reacts with the UPT-lyosphere, where sample may be labeled and flows along the flow strip for visual detection.

Example 6

An alternate embodiment is set forth in FIG. 17. As shown, a sample is introduced into a system—as described elsewhere herein. The sample is then metered, and in one branch of the system, is exposed to and mixed with a lysis buffer to liberate nucleic acid from the cellular sample. The release of the buffer and the mixing is preferably accomplished by an actuator depressing a fluid reservoir to release the buffer and by opening one or more valves or stops so as to permit the buffer to mix with the sample. Nucleic acid may be isolated—preferably by flowing the nucleic acid across a material, such as a silica membrane—capable of selectively adsorbing nucleic acids. The isolated nucleic acids are then eluted or released from the adsorbing material—typically by exposure to an alcohol solution liberated from an actuated fluid reservoir—and undergo a PCR reaction to amplify one or more nucleic acids. The amplified nucleic acids are then labeled and transported to a lateral flow strip for visualization.

In a separate branch of the system, a sample is contacted with an antibody or antigen, after which antibody- or antigen-containing sample is selectively labeled and visualized on a lateral flow strip. As shown, a given system may be configured so as to carry out two or more assays on a given sample, thus allowing for multiplexed detection of several pathogens that may exist in a particular sample.

Example 7

Figure 25:
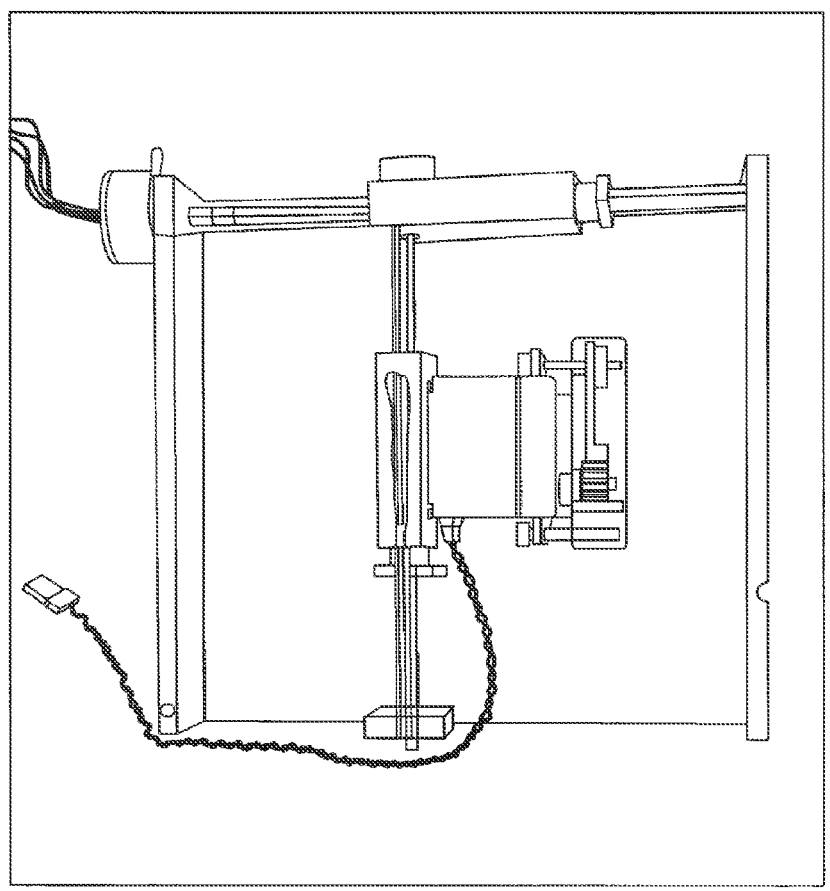
FIG. 25 illustrates a claimed device wherein the actuator of the device is a plunger capable of motion in the x-y plane.
Figure 26:
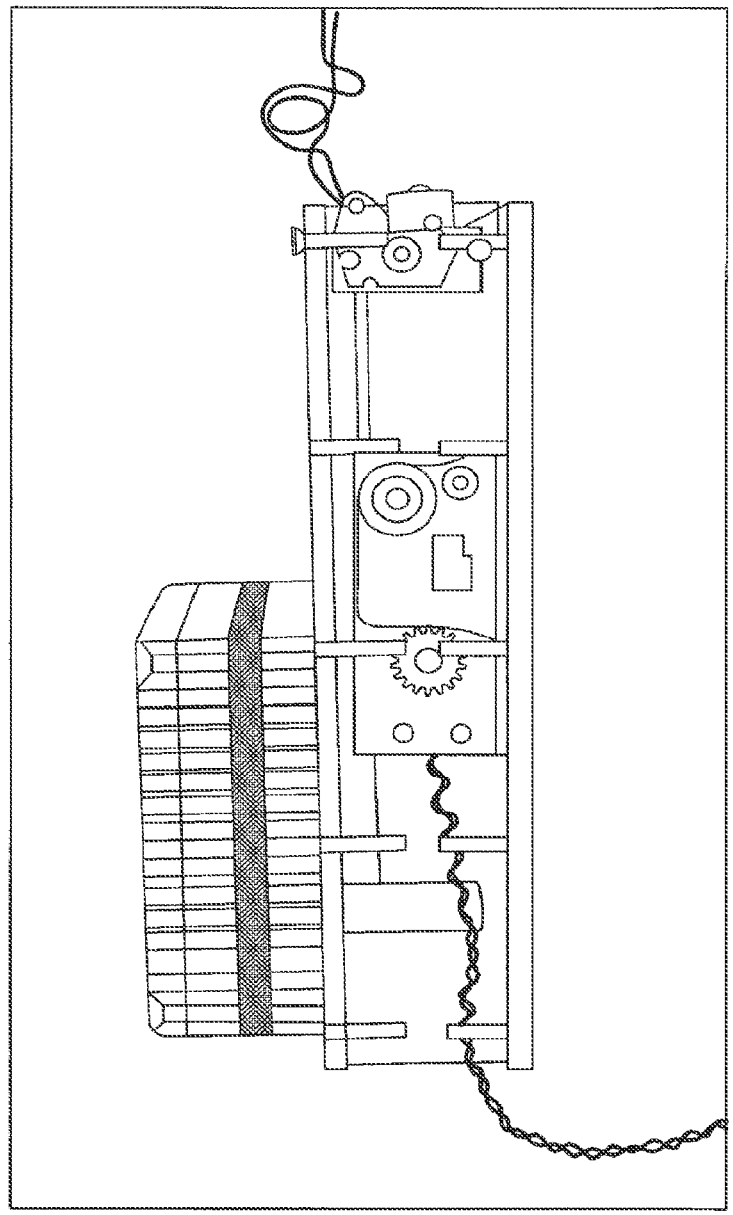
FIG. 26 illustrates a side-view of the claimed device, wherein the actuator of the device is a plunger, mounted on a stage capable of motion in the x-y plane.

A motorized stage was constructed, in which stage an actuator was mounted so as to be capable of movement in the x-y plane, as shown in FIG. 25 and FIG. 26. The actuator moves slidably on rails positioned perpendicular to one another. The movement of the actuator on the rails is accomplished by one or more gears mounted on the actuator engaging with ridges or teeth disposed on the rails. By pre-programming a set of positions into the actuator, the actuator is capable of moving to a pre-set schedule of positions, at which positions the actuator contacts a fluidic element of a cassette mounted proximate to the actuator. The actuator may include two or more pistons or plungers, thus making possible simultaneous actuation of multiple fluidic elements on a given cassette.

What is claimed:
1. A sample processing system, comprising:
 a component comprising at least one fluidic element sealed by a deformable sealing layer; and
 a moveable actuator residing proximate to the component, at least a portion of the actuator capable of motion about an axis relative to the component,
  the actuator comprising at least one protrusion spaced from the axis, and the actuator being disposed such that rotation of the actuator about the axis gives rise to motion of the at least one protrusion that effects depression of at least a portion of the deformable sealing layer, the depression actuating the at least one fluidic element.

2. The sample processing system of claim 1, wherein the protrusion comprises a ridge, a groove, an extension, an eccentricity, a depression, a ramp, a cam, or any combination thereof.

3. The sample processing system of claim 1, wherein a fluidic element comprises a conduit, a chamber, a valve, a reservoir, a mixing zone, a channel, a vent, or any combination thereof.

4. The sample processing system of claim 1, wherein the actuator comprises at least one surface residing substantially parallel to the component.

5. The sample processing system of claim 1, wherein the actuator comprises a disc that defines a top planar surface, the disc further comprising the at least one protrusion that extends from the top planar surface.

6. The sample processing system of claim 1, wherein the actuator comprises a slider bar.

7. The sample processing system of claim 1, wherein the actuator comprises at least one cam and at least one camshaft.

8. The sample processing system of claim 7, wherein the at least one protrusion extends radially outward from the at least one camshaft.

9. The sample processing system of claim 1, further comprising one or more plungers capable of actuating one or more fluidic elements.

10. A method for analyzing a sample, comprising:
placing the sample into a component comprising two or more fluidic elements in fluid communication with one another,
at least one of the two or more fluidic elements being surmounted by a deformable layer;
controllably subjecting at least a portion of the sample to one or more processing steps effected by the movement of an actuator relative to the component,
the actuator being disposed to rotate about an axis, the actuator comprising at least one protrusion spaced from the axis,
wherein at least one processing step of the one or more processing steps includes displacing fluid from the at least one of the two or more fluidic elements so as to transport the sample from the at least one of the two or more fluidic elements to at least one other fluidic element by rotating the actuator about the axis such that motion of the at least one protrusion effects depression of at least a portion of the deformable sealing layer, and
analyzing the sample for the presence of one or more analytes.

11. The sample processing system of claim 1, further comprising at least two fluidic elements sealed by a deformable sealing layer, wherein reciprocating motion of one or more actuator portions are capable of effecting mixing between the at least two fluidic elements.

12. The method of claim 10, wherein the actuator comprises a disc that defines a top planar surface, the at least one protrusion extending from the top planar surface.

13. The method of claim 10 wherein the actuator comprises a camshaft and the at least one protrusion, the at least one protrusion extending radially outward from the camshaft.

* * * * *

UNITED STATES PATENT AND TRADEMARK OFFICE
CERTIFICATE OF CORRECTION

PATENT NO. : 8,691,592 B2  Page 1 of 1
APPLICATION NO. : 12/515616
DATED : April 8, 2014
INVENTOR(S) : Chen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1204 days.

Signed and Sealed this
Twenty-ninth Day of September, 2015

Michelle K. Lee
*Director of the United States Patent and Trademark Office*